(12) United States Patent
Vakharia et al.

(10) Patent No.: US 8,568,410 B2
(45) Date of Patent: Oct. 29, 2013

(54) ELECTRICAL ABLATION SURGICAL INSTRUMENTS

(75) Inventors: Omar J. Vakharia, Cincinnati, OH (US); Kurt R. Bally, Lebanon, OH (US); Andrew M. Zwolinski, Cincinnati, OH (US); Gregory J. Bakos, Mason, OH (US); Matthew D. Holcomb, Lebanon, OH (US); Gary L. Long, Cincinnati, OH (US); Steven P. Woodard, Cupertino, CA (US); Surag S. Mantri, Sunnyvale, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1206 days.

(21) Appl. No.: 12/109,673

(22) Filed: Apr. 25, 2008

(65) Prior Publication Data

US 2009/0062792 A1   Mar. 5, 2009

Related U.S. Application Data

(63) Continuation-in-part of application No. 11/897,676, filed on Aug. 31, 2007, and a continuation-in-part of application No. 11/986,420, filed on Nov. 21, 2007, now Pat. No. 8,262,655, and a continuation-in-part of application No. 11/986,489, filed on Nov. 21, 2007.

(51) Int. Cl.
*A61B 18/12* (2006.01)

(52) U.S. Cl.
USPC .............................................. 606/51; 606/52

(58) Field of Classification Search
USPC ..................................................... 606/50–52
See application file for complete search history.

(56) References Cited

U.S. PATENT DOCUMENTS

| | | | |
|---|---|---|---|
| 645,576 A | 3/1900 | Tesla |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,031,682 A | 2/1936 | Wappler et al. |
| 2,113,246 A | 4/1938 | Wappler |

(Continued)

FOREIGN PATENT DOCUMENTS

| | | |
|---|---|---|
| AU | 666310 B2 | 2/1996 |
| DE | 3008120 A1 | 9/1980 |

(Continued)

OTHER PUBLICATIONS

K. Sumiyama et al., "Endoscopic Caps," Tech. Gastrointest. Endosc., vol. 8, pp. 28-32, 2006.

(Continued)

*Primary Examiner* — Michael Peffley
*Assistant Examiner* — Daniel Fowler

(57) ABSTRACT

An electrical ablation device includes an elongated flexible member having a proximal end and a distal end. A clamp jaw portion is located at the distal end of the elongated flexible member. The clamp jaw portion is operatively movable from an open position to a closed position. A cutting blade is located in the clamp jaw portion. The clamp jaw portion is adapted to couple to an electrical waveform generator and to receive an electrical waveform.

21 Claims, 26 Drawing Sheets

(56) References Cited

U.S. PATENT DOCUMENTS

| | | |
|---|---|---|
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |

(56) References Cited

U.S. PATENT DOCUMENTS

| | | |
|---|---|---|
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,443,463 A | 8/1995 | Stern et al. |
| 5,445,638 A | 8/1995 | Rydell et al. |
| 5,449,021 A | 9/1995 | Chikama |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A | 6/1996 | Hinchliffe |
| 5,536,248 A | 7/1996 | Weaver et al. |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A * | 5/1997 | Tihon ............................. 606/48 |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,716,326 A | 2/1998 | Dannan |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,746,759 A | 5/1998 | Meade et al. |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,824,071 A | 10/1998 | Nelson et al. |
| 5,827,281 A | 10/1998 | Levin |
| 5,827,299 A | 10/1998 | Thomason et al. |
| 5,830,231 A | 11/1998 | Geiges, Jr. |
| 5,833,700 A | 11/1998 | Fogelberg et al. |
| 5,833,703 A | 11/1998 | Manushakian |

(56) References Cited

U.S. PATENT DOCUMENTS

| | | |
|---|---|---|
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,899,919 A | 5/1999 | Eubanks, Jr. et al. |
| 5,902,254 A | 5/1999 | Magram |
| 5,904,702 A | 5/1999 | Ek et al. |
| 5,908,420 A | 6/1999 | Parins et al. |
| 5,908,429 A | 6/1999 | Yoon |
| 5,911,737 A | 6/1999 | Lee et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,944,718 A | 8/1999 | Austin et al. |
| 5,951,549 A | 9/1999 | Richardson et al. |
| 5,954,720 A | 9/1999 | Wilson et al. |
| 5,954,731 A | 9/1999 | Yoon |
| 5,957,943 A | 9/1999 | Vaitekunas |
| 5,957,953 A | 9/1999 | DiPoto et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,989,182 A | 11/1999 | Hori et al. |
| 5,993,447 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,634 A | 2/2000 | Wu et al. |
| 6,033,399 A | 3/2000 | Gines |
| 6,036,685 A | 3/2000 | Mueller |
| 6,053,927 A | 4/2000 | Hamas |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,108 A | 7/2000 | McBrayer et al. |
| 6,096,046 A | 8/2000 | Weiss |
| 6,102,926 A | 8/2000 | Tartaglia et al. |
| 6,106,473 A | 8/2000 | Violante et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,139,555 A | 10/2000 | Hart et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,156,006 A | 12/2000 | Brosens et al. |
| 6,159,200 A | 12/2000 | Verdura et al. |
| 6,165,184 A | 12/2000 | Verdura et al. |
| 6,168,570 B1 | 1/2001 | Ferrera |
| 6,168,605 B1 | 1/2001 | Measamer et al. |
| 6,170,130 B1 | 1/2001 | Hamilton et al. |
| 6,179,776 B1 | 1/2001 | Adams et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,214,007 B1 | 4/2001 | Anderson |
| 6,228,096 B1 | 5/2001 | Marchand |
| 6,234,958 B1 | 5/2001 | Snoke et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,322,578 B1 | 11/2001 | Houle et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,035 B1 | 3/2002 | Manushakian |
| 6,361,534 B1 | 3/2002 | Chen et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,391,029 B1 | 5/2002 | Hooven et al. |
| 6,402,735 B1 | 6/2002 | Langevin |
| 6,406,440 B1 | 6/2002 | Stefanchik |
| 6,409,727 B1 * | 6/2002 | Bales et al. .................. 606/47 |
| 6,409,733 B1 | 6/2002 | Conlon et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,076 B1 | 10/2002 | Pruitt |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |

(56) References Cited

U.S. PATENT DOCUMENTS

| | | |
|---|---|---|
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,520,954 B2 | 2/2003 | Ouchi |
| 6,543,456 B1 | 4/2003 | Freeman |
| 6,551,270 B1 | 4/2003 | Bimbo et al. |
| 6,554,829 B2 | 4/2003 | Schulze et al. |
| 6,558,384 B2 | 5/2003 | Mayenberger |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,638,286 B1 | 10/2003 | Burbank et al. |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |

(56) References Cited

U.S. PATENT DOCUMENTS

| | | |
|---|---|---|
| 7,115,092 B2 | 10/2006 | Park et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,152,488 B2 | 12/2006 | Hedrich et al. |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francese et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,322 B2 | 7/2008 | Wenchell |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,618,398 B2 | 11/2009 | Holman et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,674,259 B2 | 3/2010 | Shadduck |
| 7,713,189 B2 | 5/2010 | Hanke |
| 7,713,270 B2 | 5/2010 | Suzuki |
| 7,736,374 B2 | 6/2010 | Vaughan et al. |
| 7,744,615 B2 | 6/2010 | Couture |
| 7,758,577 B2 | 7/2010 | Nobis et al. |
| 7,762,949 B2 | 7/2010 | Nakao |
| 7,762,998 B2 | 7/2010 | Birk et al. |
| 7,771,416 B2 | 8/2010 | Spivey et al. |
| 7,780,683 B2 | 8/2010 | Roue et al. |
| 7,780,691 B2 | 8/2010 | Stefanchik |
| 7,794,409 B2 | 9/2010 | Damarati |
| 7,794,475 B2 | 9/2010 | Hess et al. |
| 7,828,186 B2 | 11/2010 | Wales |
| 7,837,615 B2 | 11/2010 | Le et al. |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,892,220 B2 | 2/2011 | Faller et al. |
| 7,896,887 B2 | 3/2011 | Rimbaugh et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,931,624 B2 | 4/2011 | Smith et al. |
| 7,945,332 B2 | 5/2011 | Schechter |
| 7,947,000 B2 | 5/2011 | Vargas et al. |
| 7,955,298 B2 | 6/2011 | Carroll et al. |
| 7,963,975 B2 | 6/2011 | Criscuolo |
| 7,988,685 B2 | 8/2011 | Ziaie et al. |
| 8,075,587 B2 | 12/2011 | Ginn |
| 8,088,062 B2 | 1/2012 | Zwolinski |
| 8,118,821 B2 | 2/2012 | Mouw |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2002/0188294 A1* | 12/2002 | Couture et al. .......... 606/51 |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114732 A1 | 6/2003 | Webler et al. |
| 2003/0120257 A1 | 6/2003 | Houston et al. |

(56) References Cited

U.S. PATENT DOCUMENTS

| | | |
|---|---|---|
| 2003/0124009 A1 | 7/2003 | Ravi et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0002735 A1 | 1/2004 | Lizardi et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |

(56) References Cited

U.S. PATENT DOCUMENTS

| | | |
|---|---|---|
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247576 A1 | 11/2006 | Poncet |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106118 A1 | 5/2007 | Moriyama |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260273 A1 | 11/2007 | Cropper et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0147113 A1 | 6/2008 | Nobis et al. |
| 2008/0171907 A1 | 7/2008 | Long et al. |
| 2008/0177135 A1 | 7/2008 | Muyari et al. |

(56) References Cited

U.S. PATENT DOCUMENTS

| | | |
|---|---|---|
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200912 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0054728 A1 | 2/2009 | Trusty |
| 2009/0062788 A1 | 3/2009 | Long et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0216248 A1 | 8/2009 | Uenohara et al. |
| 2009/0227828 A1 | 9/2009 | Swain et al. |
| 2009/0248055 A1 | 10/2009 | Spivey et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Splvey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0249700 A1 | 9/2010 | Spivey |
| 2010/0261994 A1 | 10/2010 | Davalos et al. |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0106221 A1 | 5/2011 | Neal, II et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0245619 A1 | 10/2011 | Holcomb |
| 2011/0306971 A1 | 12/2011 | Long |
| 2012/0004502 A1 | 1/2012 | Weitzner et al. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0116155 A1 | 5/2012 | Trusty |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |

(56) References Cited

FOREIGN PATENT DOCUMENTS

| | | |
|---|---|---|
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 1493397 B1 | 9/2011 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2000245683 A | 9/2000 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2006297005 A | 11/2006 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A1 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/080974 A1 | 7/2010 |
| WO | WO 2010/088481 A1 | 8/2010 |

OTHER PUBLICATIONS

F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La

(56) References Cited

OTHER PUBLICATIONS

Societe Royale De Medecin De Marseille. Marseille: Impr. D'Achard, 1826; 1:127-31. (with English translation).
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. (2007), pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRe1Id=1000.1003&method=D . . . , accessed Jul. 18, 2008 (4 pages).
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 11/756,914, filed Jun. 1, 2007.
U.S. Appl. No. 12/060,601, filed Apr. 1, 2008.
Partial International Search Report for PCT/US2008/074299, Feb. 27, 2009 (2 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
U.S. Appl. No. 11/952,475, filed Dec. 7, 2007.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 11/706,591, filed Feb. 15, 2007.
U.S. Appl. No. 11/706,766, filed Feb. 15, 2007.
U.S. Appl. No. 11/897,676, filed Aug. 31, 2007.
U.S. Appl. No. 11/986,420, filed Nov. 21, 2007.
U.S. Appl. No. 11/986,489, filed Nov. 21, 2007.
Michael S. Kavic, M.D., "Natural Orifice Translumenal Endoscopic Surgery: "NOTES"", JSLS, vol. 10, pp. 133-134 (2006).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With The Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
"Z-Offset Technique Used in the Introduction of Trocar During Laparoscopic Surgery," M.S. Hershey NOTES Presentation to EES NOTES Development Team, Sep. 27, 2007.
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastomosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

(56) References Cited

OTHER PUBLICATIONS

U.S. Appl. No. 11/706,460, filed Feb. 15, 2007.
U.S. Appl. No. 11/706,685, filed Feb. 15, 2007.
U.S. Appl. No. 11/706,811, filed Feb. 15, 2007.
U.S. Appl. No. 11/707,831, filed Feb. 16, 2007.
U.S. Appl. No. 11/715,710, filed Mar. 8, 2007.
U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
International Search Report and Written Opinion for PCT/US2008/074299, Dec. 12, 2009 (20 pages).
International Preliminary Report on Patentability for PCT/US2008/074299, Mar. 11, 2010 (10 pages).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented At DDW Demonstrate Potential Of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles/.view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.
U.S. Appl. No. 13/420,805, filed Mar. 15, 2012.
U.S. Appl. No. 13/420,818, filed Mar. 15, 2012.
U.S. Appl. No. 13/425,103, filed Mar. 20, 2012.

\* cited by examiner

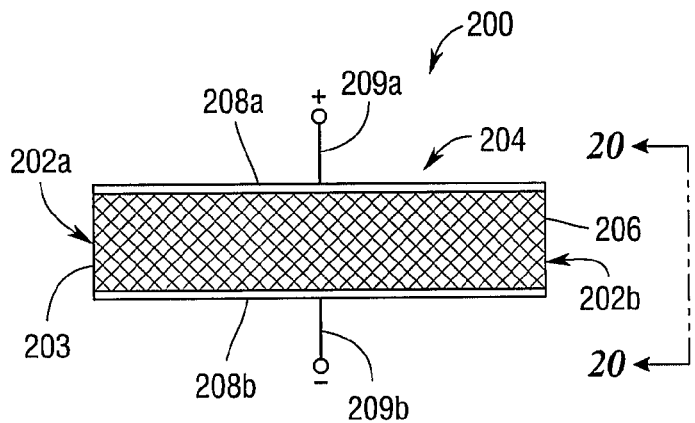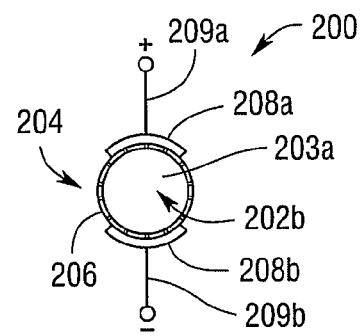
*Fig.19*  *Fig.20*
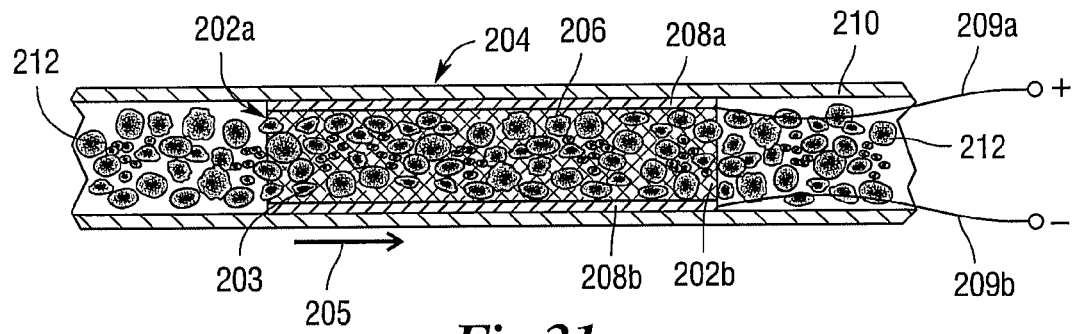
*Fig.21*
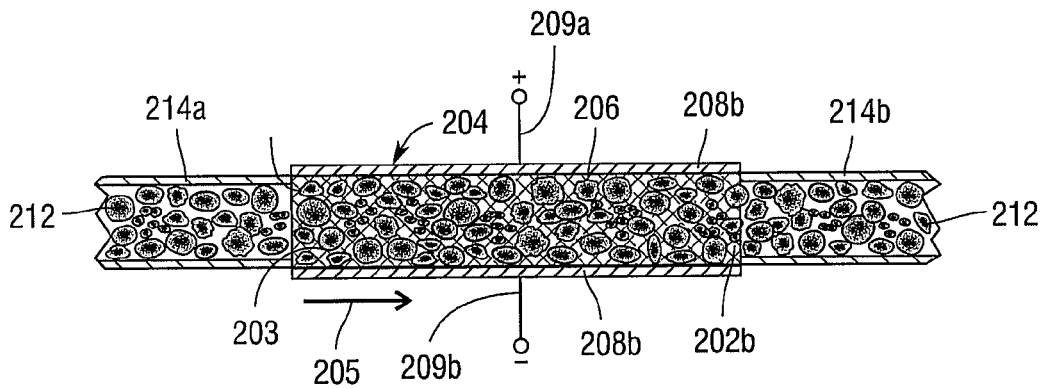
*Fig.22*

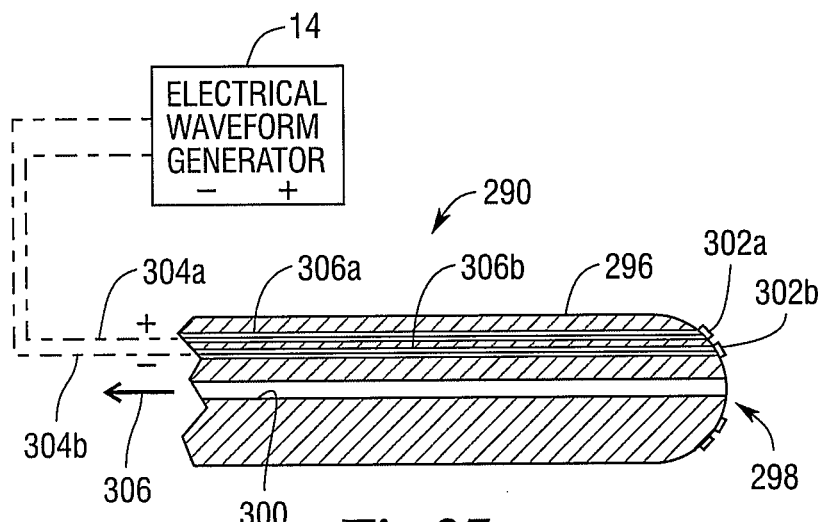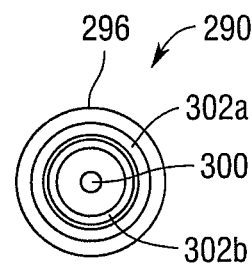
*Fig.27*  *Fig.28*
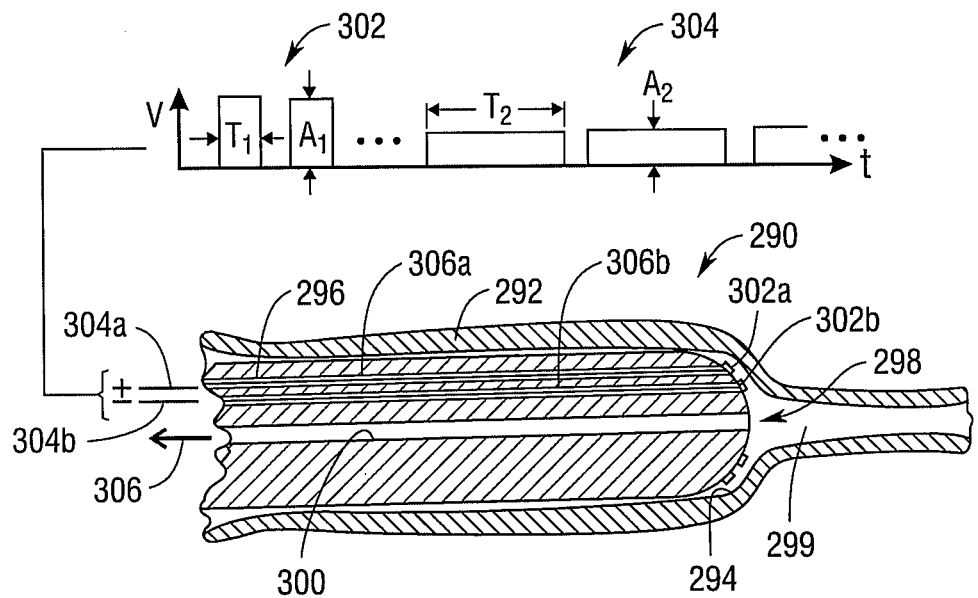
*Fig.29*

ELECTRICAL ABLATION SURGICAL INSTRUMENTS

CROSS-REFERENCE TO RELATED APPLICATIONS

This application is a continuation-in-part application of application Ser. No. 11/897,676, filed Aug. 31, 2007, now U.S. Publication No. 2009/0062788, titled "ELECTRICAL ABLATION SURGICAL INSTRUMENTS"; a continuation-in-part application of application Ser. No. 11/986,420, filed Nov. 21, 2007, now U.S. Pat. No. 8,262,655, titled "BIPOLAR FORCEPS"; and a continuation-in-part application of application Ser. No. 11/986,489, filed Nov. 21, 2007, now U.S. Publication No. 2009/0131932, titled "BIPOLAR FORCEPS HAVING A CUTTING ELEMENT"; the disclosure of each of these applications is incorporated herein by reference in its entirety.

BACKGROUND

Electrical therapy techniques have been employed in medicine to treat pain and other conditions. Electrical ablation techniques have been employed in medicine to remove diseased tissue or abnormal growths, such as cancers or tumors, from the body. Electrical therapy probes comprising electrodes are employed to electrically treat diseased tissue at the tissue treatment region or target site. These electrical therapy probes comprising electrodes are usually inserted into the tissue treatment region percutaneously. There is a need for minimally invasive flexible endoscopic, laparoscopic, or thoracoscopic electrical ablation devices and methods to access a tissue treatment region, e.g., in the lungs or liver, to diagnose and treat diseased tissue more accurately and effectively using minimally invasive surgical methods. There is a need for improved flexible endoscopic, laparoscopic, or thoracoscopic electrical ablation devices that can be introduced into the tissue treatment region through a natural opening of the body or through a trocar inserted through a small incision formed in the body. There is a need for flexible endoscopic, laparoscopic, or thoracoscopic electrical ablation devices that include a cutting device to transect a targeted vessel. There is also a need for flexible endoscopic, laparoscopic, or thoracoscopic electrical ablation devices to thermally seal the targeted vessel using electrical energy prior to transecting the targeted vessel with the cutting device.

SUMMARY

In one general aspect, the various embodiments are directed to electrical ablation devices. In one embodiment, an electrical ablation device comprises an elongated flexible member having a proximal end and a distal end. A clamp jaw portion is located at the distal end of the elongated flexible member. The clamp jaw portion is operatively movable from an open position to a closed position. A cutting blade is located in the clamp jaw portion. The clamp jaw portion is adapted to couple to an electrical waveform generator and to receive an electrical waveform.

FIGURES

The novel features of the various embodiments are set forth with particularity in the appended claims. The various embodiments, however, both as to organization and methods of operation, together with further advantages thereof, may best be understood by reference to the following description, taken in conjunction with the accompanying drawings as follows.

FIG. 1 illustrates one embodiment of an electrical ablation system.

FIGS. 2A-D illustrate one embodiment of the electrical ablation device of the electrical ablation system shown in FIG. 1 in various phases of deployment.

FIG. 4 is a perspective side view of one embodiment of an electrical ablation device.

FIG. 5 is a side view of one embodiment of the electrical ablation device shown in FIG. 4.

FIG. 6 is a cross-sectional perspective view of one embodiment of the electrical ablation device taken across line 6-6 in FIG. 4.

FIG. 7 is a cross-sectional perspective view of one embodiment of the electrical ablation device taken across line 7-7 in FIG. 4.

FIG. 8 is a front view of one embodiment of the electrical ablation device taken along line 8-8 in FIG. 5.

FIG. 9 is a back view of one embodiment of the electrical ablation device taken along line 9-9 in FIG. 5.

FIG. 10 is a cross-sectional view of one embodiment of the electrical ablation device taken along the longitudinal axis.

FIG. 12 is a top side perspective side view of the electrical ablation device.

FIG. 13 is a bottom side perspective view of one embodiment of the electrical ablation device shown in FIG. 12.

FIG. 14 is a side view of one embodiment of the electrical ablation device shown in FIG. 12.

FIG. 15 is a front view of one embodiment of the electrical ablation device taken along line 15-15 in FIG. 14.

FIG. 16 is a cross-sectional view of one embodiment of the electrical ablation device taken along the longitudinal axis.

FIG. 17 is a perspective view of one embodiment of the electrical ablation device with a handle assembly coupled to thereto.

FIG. 18 is a cross-sectional view of one embodiment of the right-hand portion of the handle assembly.

FIG. 19 illustrates one embodiment of an electrical ablation device.

FIG. 20 is an end view of one embodiment of the electrical ablation device shown in FIG. 19 taken along line 20-20.

FIG. 21 illustrates one embodiment of the electrical ablation device shown in FIG. 19 implanted in a blood vessel of a patient.

FIG. 22 illustrates one embodiment of the electrical ablation device shown in FIG. 19 located external to a patient.

FIGS. 27, 28, and 29 illustrate one embodiment of an electrical ablation device to treat diseased tissue within a body lumen using electrical energy.

FIG. 27 illustrates a sectioned view of one embodiment of an electrical ablation probe.

FIG. 28 illustrates an end view of one embodiment of the electrical ablation probe shown in FIG. 27.

FIG. 29 is a cross-sectional view of one embodiment of the electrical ablation probe that may be inserted in a lumen within a vessel.

Figure 30:
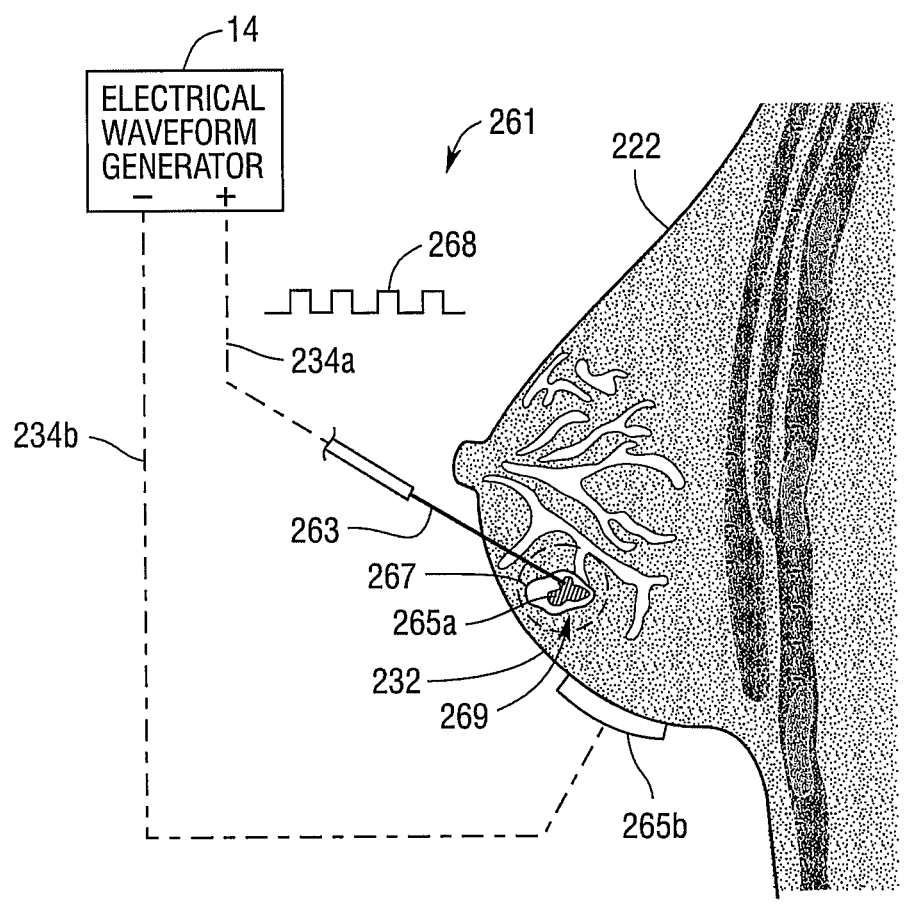

FIG. 30 illustrates one embodiment of an electrical ablation device to treat diseased tissue within a breast by delivering electrical energy to a space defined within the breast.

Figure 31:
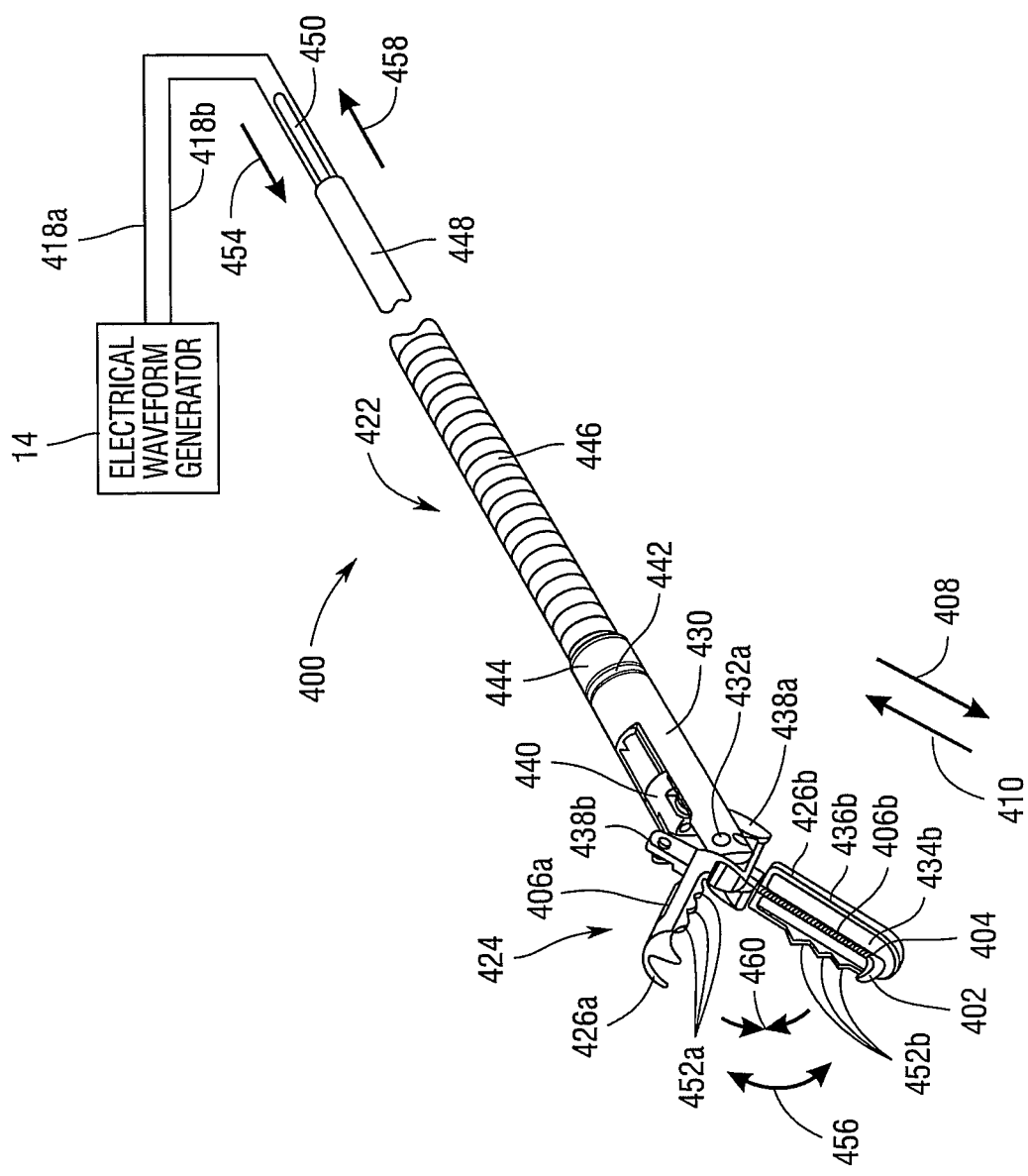

FIG. 31 is a perspective side view of one embodiment of an electrical ablation device comprising a cutting blade.

Figure 32:
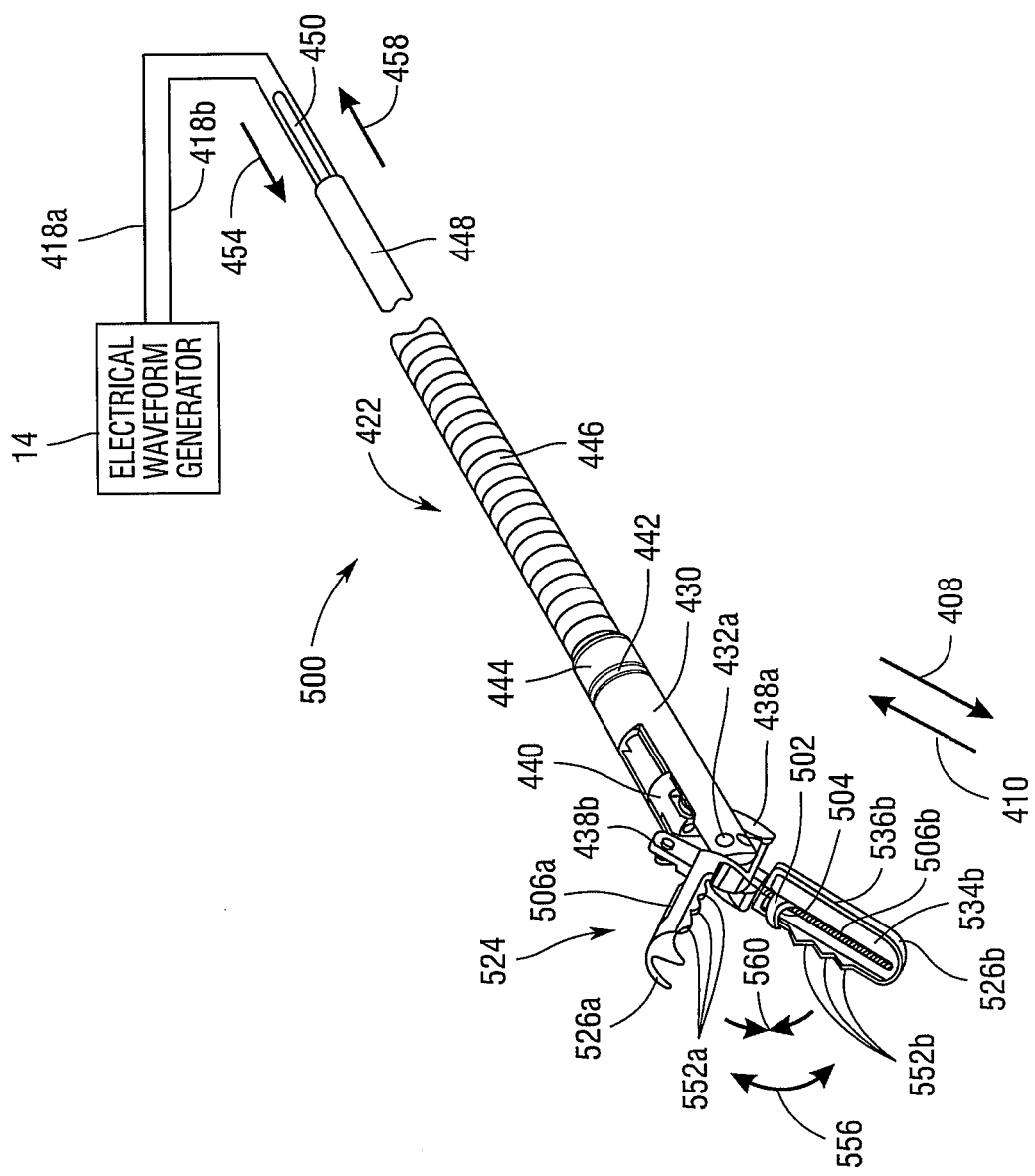

FIG. 32 is a perspective side view of one embodiment of an electrical ablation device comprising a cutting blade.

Figure 33:
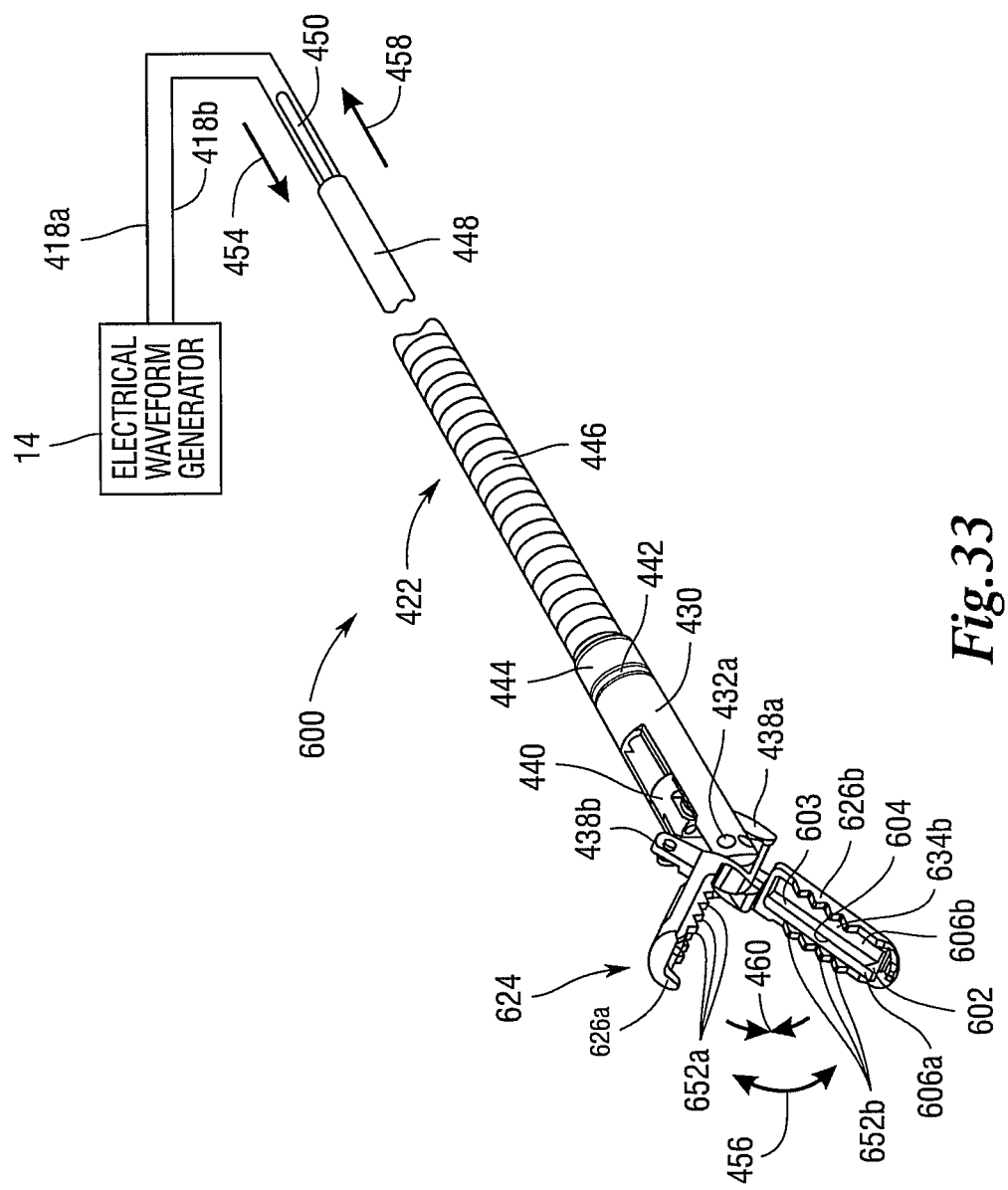

FIG. 33 is a perspective side view of one embodiment of an electrical ablation device comprising a cutting blade.

Figure 34:
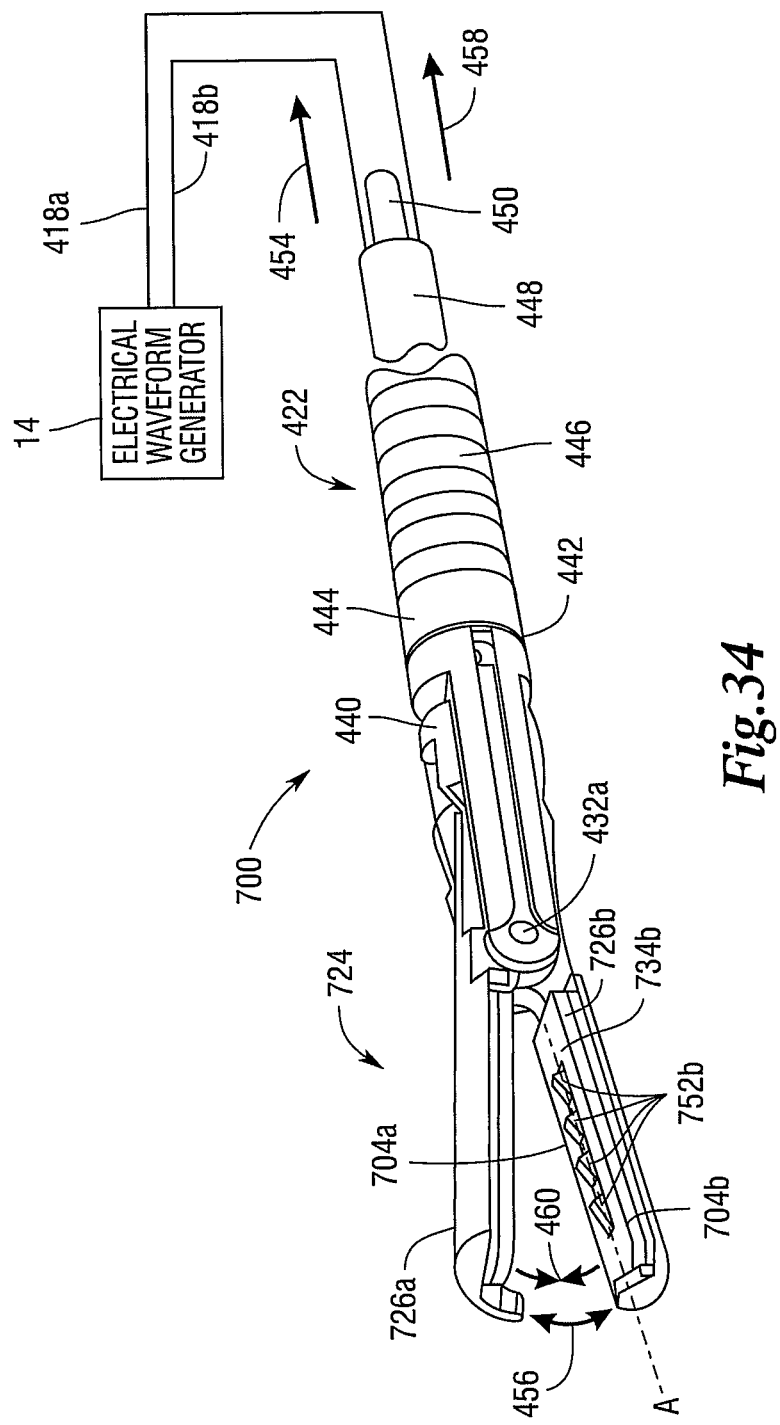

FIG. 34 is a perspective side view of one embodiment of an electrical ablation device.

DESCRIPTION

The various embodiments described herein are directed to electrical therapy ablation devices. The electrical therapy ablation devices comprise probes and electrodes that can be positioned in or in proximity to a tissue treatment region (e.g., target site) within a patient either endoscopically or transcutaneously (percutaneously), and, in some embodiments, a combination thereof. An electrode may be introduced into the tissue treatment region through a trocar. Other electrodes may be introduced in the tissue treatment region transcutaneously or percutaneously. The electrodes comprise an electrically conductive portion with a sharp point to facilitate insertion through the skin of a patient and to enhance local current density in the tissue treatment region during the treatment. Other electrodes may be introduced in the tissue treatment region by way of a natural orifice through a cannula or catheter. The placement and location of the electrodes can be important for effective and efficient therapy. Once positioned, the electrical therapy electrodes are adapted to deliver electrical current to the treatment region. The electrical current is generated by a control unit or generator located external to the patient. The electrical current may be characterized by a particular waveform in terms of frequency, amplitude, and pulse width. Depending on the diagnostic or therapeutic treatment rendered, the probes may comprise one electrode containing both a cathode and an anode or may contain a plurality of electrodes with at least one serving as a cathode and at least one serving as an anode.

Electrical therapy ablation may employ electroporation or electropermeabilization techniques where an externally applied electric field (electric potential) significantly increases the electrical conductivity and permeability of a cell plasma membrane. Electroporation is the generation of a destabilizing electric potential across such biological membranes. In electroporation, pores are formed when the voltage across the cell plasma membrane exceeds its dielectric strength. Electroporation destabilizing electric potentials are generally in the range of several hundred volts across a distance of several millimeters. Below certain magnitude thresholds, the electric potentials may be applied across a biological membrane as a way of introducing some substance into a cell, such as loading it with a molecular probe, a drug that can change the function of the cell, a piece of coding DNA, or increasing the uptake of drugs in cells. If the strength of the applied electrical field and/or duration of exposure to it are suitably chosen, the pores formed by the electrical pulse reseal after a short period of time; during such period, extracellular compounds may enter into the cell. Below a certain field threshold, the process is reversible and the potential does not permanently damage the cell membrane. This process may be referred to as reversible electroporation (RE).

On the other hand, excessive exposure of live cells to large electric fields can cause apoptosis and/or necrosis—the processes that result in cell death. Excessive exposure of live cells to large excessive electrical fields or potentials across the cell membranes causes the cells to die and, therefore, may be referred to as irreversible electroporation (IRE).

Electroporation may be performed with devices called electroporators. These appliances create the electric current and send it through the cell. Electroporators may comprise two or more metallic (e.g., aluminum) electrically conductive electrodes connected to an energy source. The energy source generates an electric field having a suitable characteristic waveform output in terms of frequency, amplitude, and pulse width.

Endoscopy refers to looking inside the human body for medical reasons. Endoscopy may be performed using an instrument called an endoscope. Endoscopy is a minimally invasive diagnostic medical procedure used to evaluate the interior surfaces of an organ by inserting a small tube into the body, often, but not necessarily, through a natural body opening or through a relatively small incision. Through the endoscope, an operator may observe surface conditions of the organs, including abnormal or diseased tissue such as lesions and other surface conditions. The endoscope may have a rigid or a flexible tube and, in addition to providing an image for visual inspection and photography, the endoscope may be adapted and configured for taking biopsies, retrieving foreign objects, and introducing medical instruments to a tissue treatment region referred to as the target site. Endoscopy is a vehicle for minimally invasive surgery.

Laparoscopic surgery is a minimally invasive surgical technique in which operations in the abdomen are performed through small incisions (usually 0.5-1.5 cm), keyholes, as compared to larger incisions needed in traditional surgical procedures. Laparoscopic surgery includes operations within the abdominal or pelvic cavities, whereas keyhole surgery performed on the thoracic or chest cavity is called thoracoscopic surgery. Laparoscopic and thoracoscopic surgery belong to the broader field of endoscopy.

A key element in laparoscopic surgery is the use of a laparoscope: a telescopic rod lens system that is usually connected to a video camera (single chip or three chip). Also attached is a fiber-optic cable system connected to a "cold" light source (halogen or xenon), to illuminate the operative field, inserted through a 5 mm or 10 mm cannula to view the operative field. The abdomen is usually insufflated with carbon dioxide gas to create a working and viewing space. The abdomen is essentially blown up like a balloon (insufflated), elevating the abdominal wall above the internal organs like a dome. Carbon dioxide gas is used because it is common to the human body and can be removed by the respiratory system if it is absorbed through tissue.

The embodiments of the electrical therapy ablation devices and techniques described herein may be employed to treat diseased tissue, tissue masses, tissue tumors, and lesions (diseased tissue) at a tissue treatment region (target site) within the body. The embodiments of the electrical therapy ablation devices and techniques described herein may be adapted to provide minimally invasive access to the tissue treatment region or anatomic location, such as lung and liver tissue, for example, to diagnose and treat the condition at the tissue treatment region more accurately and effectively. Such minimally invasive devices may be introduced into the tissue treatment region using a trocar. Once located at the target site, the diseased tissue is electrically ablated or destroyed. Some portions of the electrical therapy ablation devices may be inserted into the tissue treatment region percutaneously. Other portions of the electrical therapy ablation devices may be introduced in the tissue treatment region endoscopically (e.g., laparoscopically and/or thoracoscopically) or through small incisions. The electrical therapy ablation devices may be employed to deliver energy to the diseased tissue to ablate or destroy tumors, masses, lesions, and other abnormal tissue growths. In one embodiment, the electrical therapy ablation devices and techniques described herein may be employed in the treatment of cancer by quickly creating necrosis and destroying live cancerous tissue in-vivo. Minimally invasive therapeutic procedures to treat diseased tissue by introducing medical instruments to a tissue treatment region through a natural opening of the patient are known as Natural Orifice Translumenal Endoscopic Surgery (NOTES™).

Figure 1:
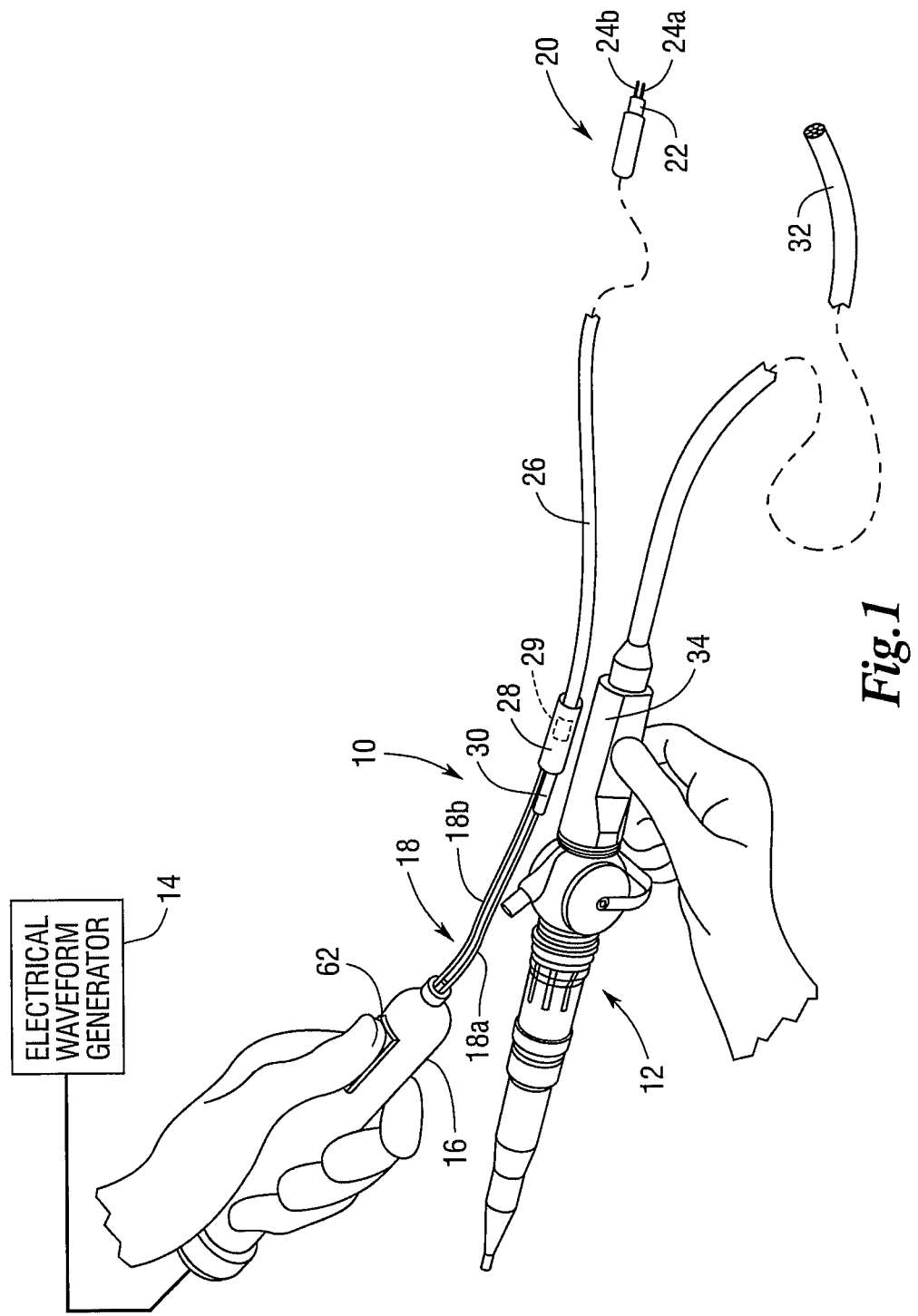

FIG. 1 illustrates one embodiment of an electrical ablation system 10. The electrical ablation system 10 may be employed to treat diseased tissue, such as tumors and lesions inside a patient, with electrical energy. The electrical ablation system 10 may be used to treat the desired tissue treatment region in endoscopic, laparoscopic, thoracoscopic, or open surgical procedures via small incisions or keyholes as well as external and noninvasive medical procedures. The electrical ablation system 10 may be configured to be positioned within a natural opening of the patient, such as the colon or the esophagus, and can be passed through the natural opening to reach the tissue treatment region or target site. The electrical ablation system 10 also may be configured to be positioned through a small incision or keyhole in the patient and can be passed through the incision to reach a tissue treatment region or target site through a trocar. The tissue treatment region may be located in the esophagus, colon, liver, breast, brain, lung, and other organs or locations within the body. The electrical ablation system 10 can be configured to treat a number of lesions and ostepathologies comprising metastatic lesions, tumors, fractures, infected site, inflamed sites, and the like. Once positioned in the tissue treatment region, the electrical ablation system 10 can be configured to treat and ablate the diseased tissue in that region. In one embodiment, the electrical ablation system 10 may be adapted to treat diseased tissue, such as cancers, of the gastrointestinal (GI) tract, esophagus, or lung that may be accessed orally. In another embodiment, the electrical ablation system 10 may be adapted to treat diseased tissue, such as cancers, of the liver or other organs that may be accessible transanally through the colon and/or the abdomen via well-known procedures.

In one embodiment, the electrical ablation system 10 may be employed in conjunction with a flexible endoscope 12 (also referred to as endoscope 12), such as the GIF-100 model available from Olympus Corporation. In one embodiment, the flexible endoscope 12, laparoscope, or thoracoscope may be introduced into the patient transanally through the colon, the abdomen via an incision or keyhole and a trocar, or through the esophagus. The endoscope 12 or laparoscope assists the surgeon to guide and position the electrical ablation system 10 near the tissue treatment region to treat diseased tissue in organs such as the liver. In another embodiment, the flexible endoscope 12 or thoracoscope may be introduced into the patient orally through the esophagus to assist the surgeon guide and position the electrical ablation system 10 near the tissue treatment region to treat diseased tissue near the gastrointestinal (GI) tract, esophagus, or lung.

In the embodiment illustrated in FIG. 1, the flexible endoscope 12 comprises an endoscope handle 34 and an elongated relatively flexible shaft 32. The distal end of the flexible shaft 32 of the flexible endoscope 12 may comprise a light source, a viewing port, and an optional working channel. The viewing port transmits an image within its field of view to an optical device such as a charge coupled device (CCD) camera within the flexible endoscope 12 so that an operator may view the image on a display monitor (not shown).

The electrical ablation system 10 generally comprises an electrical ablation device 20, a plurality of electrical conductors 18, a handpiece 16 comprising an activation switch 62, and an electrical waveform generator 14 coupled to the activation switch 62 and the electrical ablation device 20. The electrical ablation device 20 comprises a relatively flexible member or shaft 22 that may be introduced to the tissue treatment region through a trocar.

One or more needle electrodes, such as first and second electrical therapy needle electrodes 24a,b, extend out from the distal end of the electrical ablation device 20. In one embodiment, the first needle electrode 24a is the negative electrode and the second needle electrode 24b is the positive electrode. The first needle electrode 24a is electrically connected to a lead such as a first electrical conductor 18a and is coupled to the negative terminal of the electrical waveform generator 14. The second needle electrode 24b is electrically connected to a lead such as a second electrical conductor 18b and is coupled to the positive terminal of the electrical waveform generator 14. Once located in the tissue treatment region, the needle electrodes 24a,b deliver electrical energy of a predetermined characteristic shape, amplitude, frequency, and duration as supplied by the electrical waveform generator 14.

A protective sleeve or sheath 26 is slidably disposed over the flexible shaft 22 and within a handle 28 portion. The sheath 26 is slideable and may be located over the needle electrodes 24a,b to protect the trocar when the electrical ablation device 20 is pushed therethrough. Either one or both of the needle electrodes may be adapted and configured in the electrical ablation device 20 to slidably move in and out of a cannula or lumen formed within a flexible shaft 22. In the illustrated embodiments, the first needle electrode 24a, the negative electrode, can be slidably moved in and out of the distal end of the flexible shaft 22 using a slide member 30 to retract and/or advance the first needle electrode 24a. The second needle electrode 24b, the positive electrode, is fixed in place. The second needle electrode 24b provides a pivot about which the first needle electrode 24a can be moved in an arc to other points in the tissue treatment region to treat large portions of diseased tissue that cannot be treated by fixing the first and second needle electrodes 24a,b in one location. The first and second electrical conductors 18a,b are provided through a handle 28 portion. The first electrical conductor 18a, which is coupled to the first needle electrode 24a, is coupled to the slide member 30. The slide member 30 is employed to advance and retract the first needle electrode 24a, which is slidably movable within a lumen formed within the flexible shaft 22. This is described in more detail in FIGS. 2A-D.

The electrical ablation device 20 may be introduced to the desired tissue treatment region in endoscopic, laparoscopic, thoracoscopic, or open surgical procedures, as well as external and noninvasive medical procedures. Once the first and second needle electrodes 24a,b are located at respective first and second positions in the tissue treatment region, manual operation of the switch 62 of the handpiece 16 electrically connects or disconnects the needle electrodes 24a,b to the electrical waveform generator 14. Alternatively, the switch 62 may be mounted on, for example, a foot switch (not shown). The needle electrodes 24a,b may be referred to herein as endoscopic or laparoscopic electrodes. As previously discussed, either one or both of the needle electrodes 24a,b may be adapted and configured in the electrical ablation device 20 to slidably move in and out of a cannula or lumen formed within a flexible shaft 22.

In various other embodiments, transducers or sensors 29 may be located in the handle 28 portion of the electrical ablation device 20 to sense the force with which the needle electrodes 24a,b penetrate the tissue in the tissue treatment zone. This feedback information may be useful to determine whether either one or both of the needle electrodes 24a,b have been inserted in a diseased tissue region. As is well-known, cancerous tumors tend to be denser than healthy tissue and thus would require greater force to insert the needle electrodes 24a,b therein. The operator, surgeon, or clinician can physically sense when the needle electrodes 24a,b are placed within the tumor tissue in the tissue treatment zone. If the transducers or sensors 29 are employed, the information may be processed and displayed by circuits located either internally or externally to the electrical waveform generator 14. The sensor 29 readings may be employed to determine whether the needle electrodes 24a,b have been properly located in the tumor tissue thereby assuring that a suitable margin of error has been achieved in locating the needle electrodes 24a,b.

In one embodiment, the first and second needle electrodes 24a,b are adapted to receive electrical energy from a generator. The electrical energy conducted through the first and second needle electrodes 24a,b forms an electrical field at a distal end of the first and second needle electrodes 24a,b that is suitable to treat diseased tissue. In one embodiment, the electrical waveform generator 14 delivers the energy to generate the electrical field. The waveform generator 14 may be configured to generate electrical fields at a predetermined frequency, amplitude, polarity, and pulse width suitable to destroy diseased tissue cells. Application of the electrical field to the cell membranes destroys the diseased tissue located in a tissue treatment region by a process referred to as electrical ablation. The electrical waveform generator 14 may be configured to generate electrical fields in the form of direct current (DC) electrical pulses having a predetermined frequency, amplitude, and pulse width suitable to destroy cells in diseased tissues. The polarity of the DC pulses may be either positive or negative relative to a reference electrode. The polarity of the DC pulses may be reversed or inverted from positive-to-negative or from negative-to-positive any predetermined number of times to destroy the diseased tissue cells. For example, the DC electrical pulses may be delivered at a frequency in the range of 1-20 Hz, amplitude in the range of ±100 to ±1000 VDC, and pulse width in the range of 0.01-100 ms, for example. As an illustrative example, electrical waveforms having amplitude of ±500 VDC and pulse duration of 20 ms may be delivered at a pulse repetition rate or frequency of 10 Hz to destroy a reasonably large volume of diseased tissue. In one embodiment, the DC polarity of the electrical pulses may be reversed by the electrical waveform generator 14. The embodiments, however, are not limited in this context.

In one embodiment, the first and second needle electrodes 24a,b are adapted to receive electrical fields in the form of an IRE waveform from an IRE generator. In another embodiment, the first and second needle electrodes 24a,b are adapted to receive a radio frequency (RF) waveform from an RF generator. In one embodiment, the electrical waveform generator 14 may be a conventional, bipolar/monopolar electrosurgical IRE generator such as one of many models commercially available, including Model Number ECM 830, available from BTX Molecular Delivery Systems Boston, Mass. The IRE generator generates electrical waveforms having predetermined frequency, amplitude, and pulse width. The application of these electrical waveforms to the cell membranes of the diseased tissue causes the diseased cells to die. Thus, the IRE electrical waveforms may be applied to the cell membranes of diseased tissue in the tissue treatment region in order to kill the diseased cells and ablate the diseased tissue. IRE electrical waveforms suitable to destroy the cells of diseased tissues are generally in the form of DC electrical pulses delivered at a frequency in the range of 1-20 Hz, amplitude in the range of +100 to +1000 VDC, and pulse width in the range of 0.01-100 ms. For example, an electrical waveform having amplitude of +500 VDC and pulse duration of 20 ms may be delivered at a pulse repetition rate or frequency of 10 HZ to destroy a reasonably large volume of diseased tissue. Unlike RF ablation systems which require high powers and energy input into the tissue to heat and destroy, IRE requires very little energy input into the tissue; rather, the destruction of the tissue is caused by high electric fields. It has been determined that in order to destroy living tissue, the electrical waveforms have to generate an electric field of at least 30,000 V/m in the tissue treatment region.

The polarity of the electrodes 24a,b may be switched electronically to reverse the polarity of the cell. Unlike conventional IRE, reversing the polarity of the electrodes 24a,b may reduce the muscular contractions due to a constant electric field generated in the tissue. Accordingly, in one embodiment, the polarity of the electrical pulses may be inverted or reversed by the electrical waveform generator 14. For example, the electrical pulses initially delivered at a frequency in the range of 1-20 Hz and amplitude in the range of +100 to +1000 VDC, and pulse width in the range of 0.01-100 ms. The polarity of the electrical pulses then may be reversed such that the pulses have amplitude in the range of −100 to −1000 VDC. For example, an electrical waveform comprising DC pulses having amplitude of +500 VDC may be initially applied to the treatment region or target site and, after a predetermined period, the amplitude of the DC pulses may be reversed to −500 VDC. As previously discussed, to destroy a reasonably large volume of diseased tissue, the pulse duration may be 20 ms and may be delivered at a pulse repetition rate or frequency of 10 HZ. The embodiments, however, are not limited in this context.

In one embodiment, the electrical waveform generator 14 may comprise a RF waveform generator. The RF generator may be a conventional, bipolar/monopolar electrosurgical generator such as one of many models commercially available, including Model Number ICC 350, available from Erbe, GmbH. Either a bipolar mode or monopolar mode may be used. When using the bipolar mode with two electrodes, one electrode is electrically connected to one bipolar polarity, and the other electrode is electrically connected to the opposite bipolar polarity. If more than two electrodes are used, the polarity of the electrodes may be alternated so that any two adjacent electrodes have opposite polarities. Either the bipolar mode or the monopolar mode may be used with the illustrated embodiment of the electrical ablation system 10. When using the bipolar mode with two needle electrodes 24a,b, the first needle electrode 24a may be electrically connected to one bipolar polarity, and the second needle electrode 24b may be electrically connected to the opposite bipolar polarity (or vice versa). If more than two electrodes are used, the polarity of the needle electrodes 24a,b is alternated so that any two adjacent electrodes have opposite polarities.

In either case, a grounding pad is not needed on the patient when using the electrical waveform generator 14 (e.g., the IRE or RF) in the monopolar mode with two or more electrodes. Because a generator will typically be constructed to operate upon sensing connection of ground pad to the patient when in monopolar mode, it can be useful to provide an impedance circuit to simulate the connection of a ground pad to the patient. Accordingly, when the electrical ablation system 10 is used in monopolar mode without a grounding pad, an impedance circuit can be assembled by one skilled in the art, and electrically connected in series with either one of the needle electrodes 24a,b that would otherwise be used with a grounding pad attached to a patient during monopolar electrosurgery. Use of an impedance circuit allows use of the IRE generator in monopolar mode without use of a grounding pad attached to the patient.

Figure 2A:
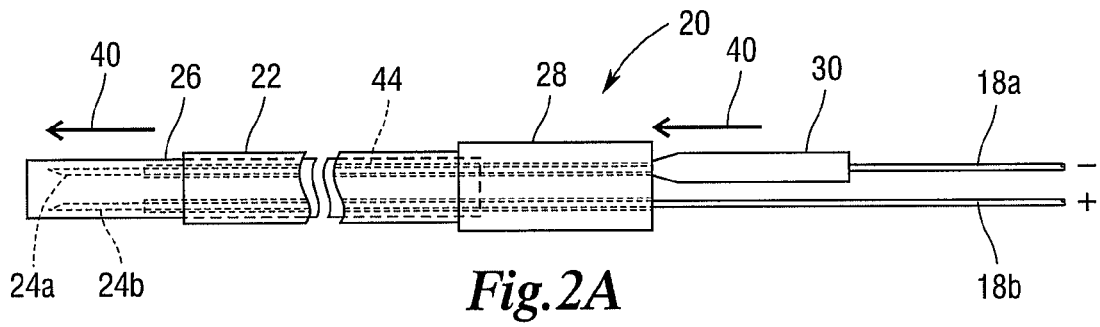
Figure 2B:
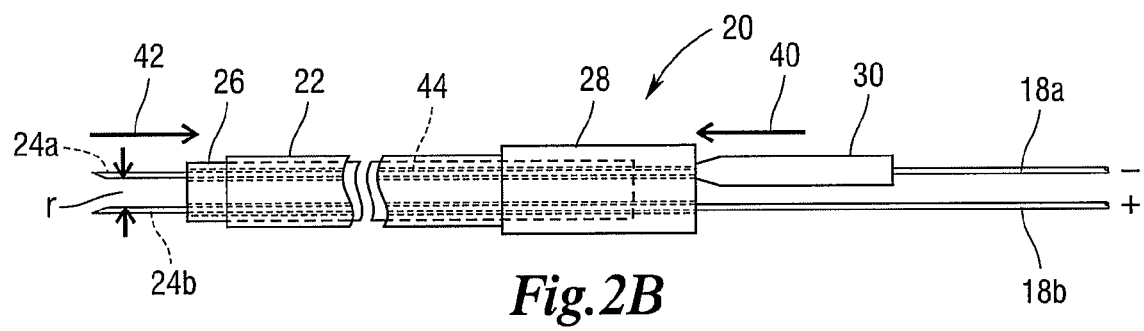
Figure 2C:
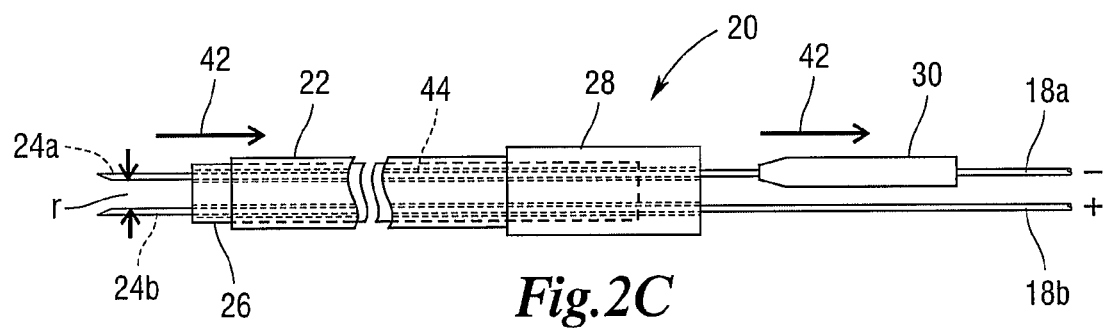
Figure 2D:
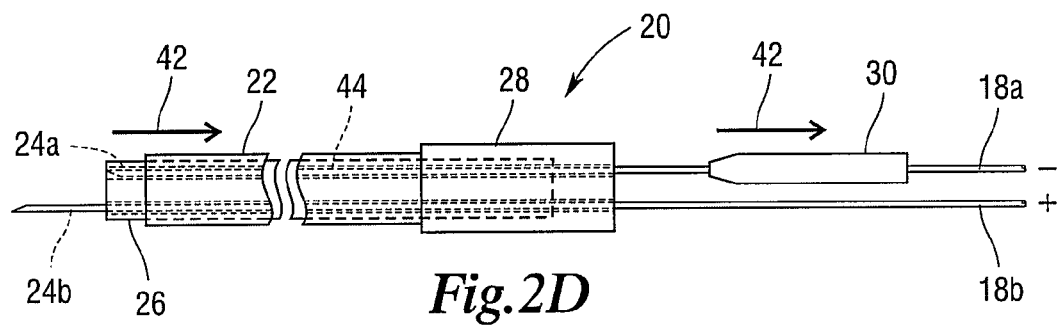

FIGS. 2A-D illustrate one embodiment of the electrical ablation device 20 of the electrical ablation system 10 shown in FIG. 1 in various phases of deployment. FIG. 2A illustrates an initial phase of deployment wherein the sheath 26 is extended in the direction indicated by arrow 40 to cover the needle electrodes 24a,b. As shown in FIG. 2A, the electrical ablation device 20 is ready to be introduced into the tissue treatment region through a trocar, for example. FIG. 2B illustrates another phase of deployment wherein the sheath 26 is retracted within the handle 28 in the direction indicated by arrow 42. In this phase of deployment the first and second needle electrodes 24a,b extend through the distal end of the flexible shaft 22 and are ready to be inserted into the tissue in the tissue treatment region. The first needle electrode 24a may be retracted in direction 42 through a lumen 44 formed in the flexible shaft 22 by holding the handle 28 and pulling on the slide member 30. FIG. 2C illustrates a transition phase wherein the first needle electrode 24a is in the process of being retracted in the direction indicated by arrow 42 by pulling on the slide member 30 handle in the same direction. FIG. 2D illustrates another phase of deployment wherein the first needle electrode 24a is in a fully retracted position. In this phase of deployment, the electrical ablation device 20 can be pivotally rotated about an axis 46 defined by the second needle electrode 24b. Once the electrical ablation device 20 is rotated in an arc about the pivot formed by the second needle electrode 24b, the first needle electrode 24a may be located in a new location in the tissue treatment region within a radius "r" defined as the distance between the first and second needle electrodes 24a,b. The needle electrodes 24a,b can be located in a plurality of positions in and around the tissue treatment region to be able to treat a much larger tissue treatment region. The first and second needle electrodes 24a,b are spaced apart by a distance "r". Spacing the first and second needle electrodes 24a,b further apart allows the electrodes to treat a larger diseased tissue region and generate an electric field over a much larger tissue treatment region. In this manner, the operator can treat a larger tissue treatment region of a cancerous lesion, a polyp, or a tumor, for example. Retracting the first needle electrode 24a and pivoting about the second needle electrode 24b enables the surgeon or clinician to target and treat a larger tissue treatment region essentially comprising a circular region having a radius "r", which is the distance between the first and second needle electrodes 24a,b.

The operator, surgeon, or clinician may employ the endoscope 12 comprising at least a light source and a viewing port located at a distal end thereof to assist in visually locating the target diseased tissue region using endoscopic visualization feedback. The needle electrodes 24a,b are energized by the electrical waveform generator 14 to deliver an IRE or an RF electrical waveform that is suitable to treat the specific diseased tissue located between the first and second needle electrodes 24a,b. Locating the needle electrodes 24a,b in the tissue treatment region independently provides the operator flexibility in positioning the needle electrodes 24a,b relative to the tissue treatment region.

The electrical conductors 18a,b are electrically insulated from each other and surrounding structures except for the electrical connections to the respective needle electrodes 24a,b. The distal end of flexible shaft 22 is proximal to the first and second needle electrodes 24a,b within the field of view of the flexible endoscope 12, thus enabling the operator to see the tissue treatment region to be treated near the first and second needle electrodes 24a,b. This technique provides a more accurate way to locate the first and second needle electrodes 24a,b in the tissue treatment region.

Figure 3:
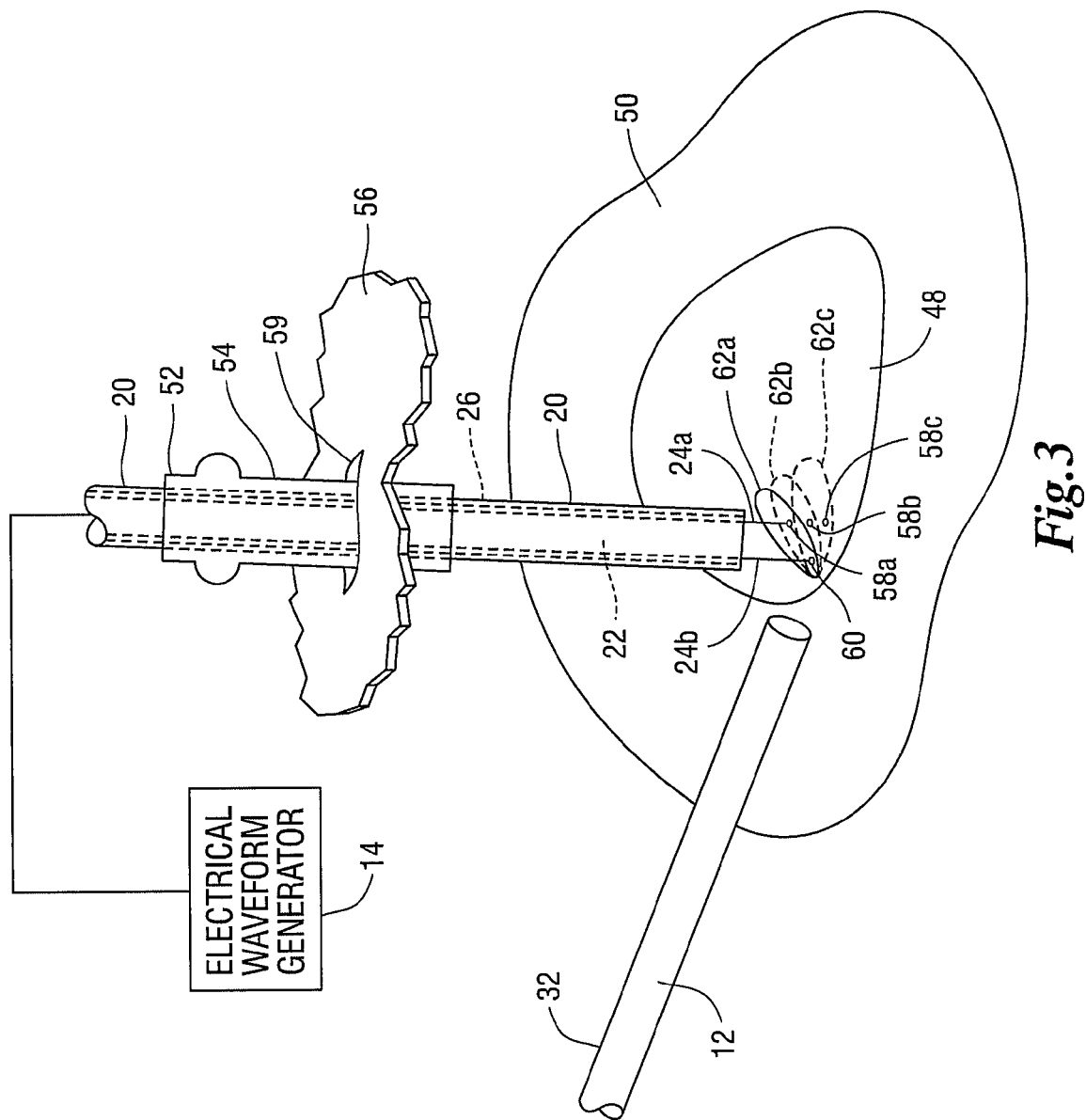
FIG. 3 illustrates the use of one embodiment of the electrical ablation system to treat diseased tissue located on the surface of the liver.

FIG. 3 illustrates the use of one embodiment of the electrical ablation system 10 to treat diseased tissue 48 located on the surface of the liver 50. In use, the electrical ablation device 20 may be introduced into the tissue treatment region through a port 52 of a trocar 54. The trocar 54 is introduced into the patient via a small incision 59 formed in the skin 56. The endoscope 12 may be introduced into the patient transanally through the colon or through a small incision or keyhole in the abdomen. The endoscope 12 is employed to guide and locate the distal end of the electrical ablation device 20 near the diseased tissue 48, otherwise referred to as the target site. Prior to introducing the flexible shaft 22 through the trocar 54, the sheath 26 is slid over the flexible shaft 22 in a direction toward the distal end thereof to cover the needle electrodes 24a,b (as shown in FIG. 2A) until the distal end of the electrical ablation device 20 reaches the diseased tissue 48 region. Once the electrical ablation device 20 has been fully introduced into the diseased tissue 48 region, the sheath 26 is retracted to expose the needle electrodes 24a,b (as shown in FIG. 2B) to treat the diseased tissue 48. The operator positions the first needle electrode 24a at a first position 58a and the second needle electrode 24b at a second position 60 using endoscopic visualization such that the diseased tissue 48 to be treated lies within the field of view of the flexible endoscope 12. The operator may locate the first needle electrode 24a located in the first position 58a near a perimeter edge of the diseased tissue 48. Once the needle electrodes 24a,b are located in the tissue treatment region and they are energized, a first necrotic zone 62a is created. For example, when the first and second needle electrodes 24a,b are placed in the desired location at positions 60 and 58a, the first and second needle electrodes 24a,b may be energized by an electrical field supplied by the electrical waveform generator 14 suitable to destroy the diseased tissue 48 in the first necrotic zone 62a. As previously discussed, the electrical field may be in the form of an IRE or RF waveform, or any electrical waveform suitable to treat the diseased tissue cells at the target site. For example, in an IRE embodiment, the first and second needle electrodes 24a,b may be energized with an electrical waveform having amplitude of approximately 500 VDC and a pulse width of approximately 20 ms at a frequency of approximately 10 Hz. In this manner, the diseased tissue 48 in the first necrotic zone 62a may be destroyed. The size of the necrotic zone is substantially dependent on the size and separation of the needle electrodes 24a,b. The treatment time is defined as the time that the needle electrodes 24a,b are activated or energized to destroy the diseased tissue. The treatment time is relatively short and may be approximately 1 or 2 seconds. Therefore, in a relatively short time, the surgeon or clinician can rapidly treat a larger treatment zone (e.g., create a larger necrotic zone) by repositioning or relocating the first needle electrode 24a within the diseased tissue region 48.

This procedure may be repeated to destroy relatively larger portions of the diseased tissue 48. The position 60 is a pivot point about which the first needle electrode 24a may be rotated in an arc of radius "r", which is the distance between the first and second electrodes 24a,b. Prior to rotating about the second needle electrode 24b, the first needle electrode 24a is retracted by pulling on the slide member 30 (FIGS. 1 and 2A-D) in a direction toward the proximal end and rotating the electrical ablation device 20 about the pivot point formed at position 60 by the second needle electrode 24b. Once the first needle electrode 24a is rotated to a second position 58b, it is advanced to engage the diseased tissue at point 58b by pushing on the slide member 30 in a direction towards the distal end. A second necrotic zone 62b is formed upon energizing the first and second electrodes 24a,b in the new location. A third necrotic zone 62c is formed by retracting the first needle electrode 24a, pivoting about pivot point 60 and rotating the first needle electrode 24a to a new location, advancing the first needle electrode 24a into the diseased tissue 48 and energizing the first and second electrodes 24a,b. This process may be repeated as often as necessary to create any number of necrotic zones 62n within multiple circular areas of radius "r", for example, that is suitable to destroy the entire diseased tissue 48 region, where n is any positive integer. At any time, the surgeon or clinician can reposition both the first and second needle electrodes 24a,b and begin the process anew. Those skilled in the art will appreciate that similar techniques may be employed to treat other diseased tissue that may be accessed transanally, through the colon and/or the abdomen, and/or accessed orally through the esophagus and/or the stomach. The embodiments, however, are not limited in this context.

Figure 4:
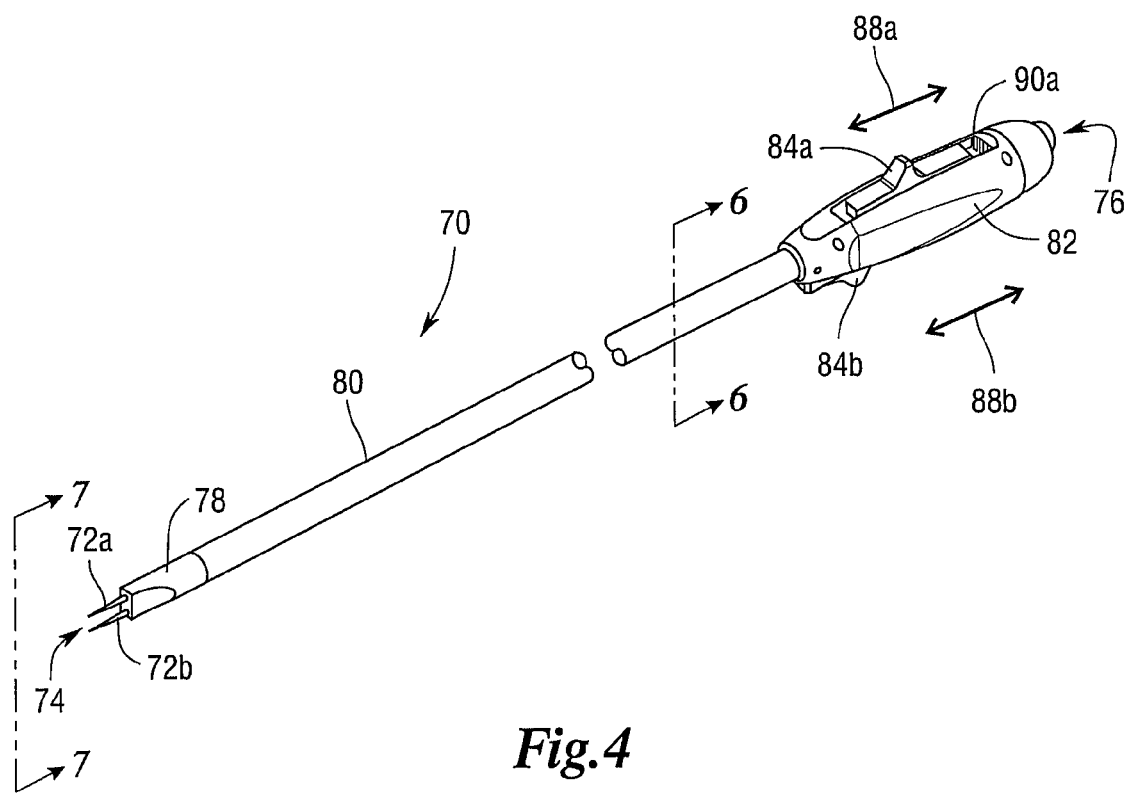
FIGS. 4-10 illustrate one embodiment of an electrical ablation device.
Figure 5:
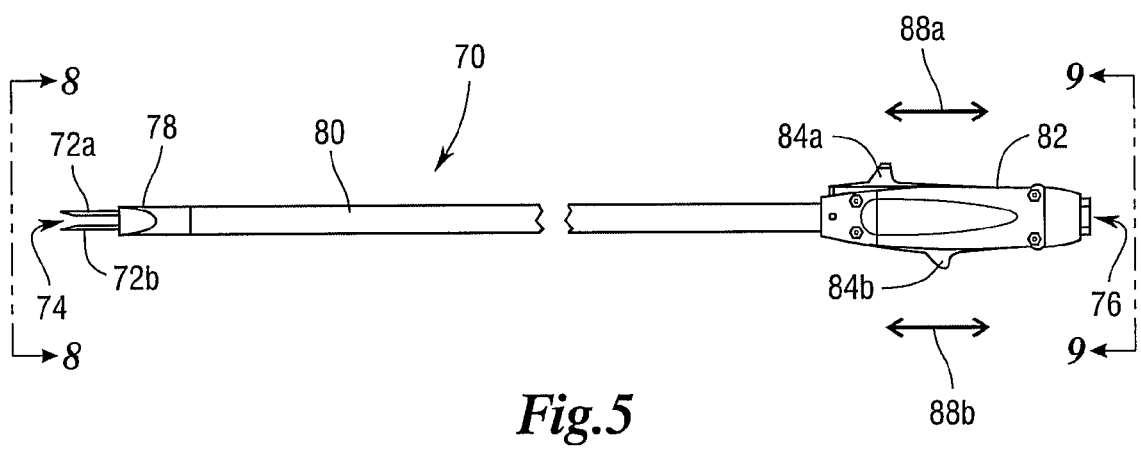
Figure 6:
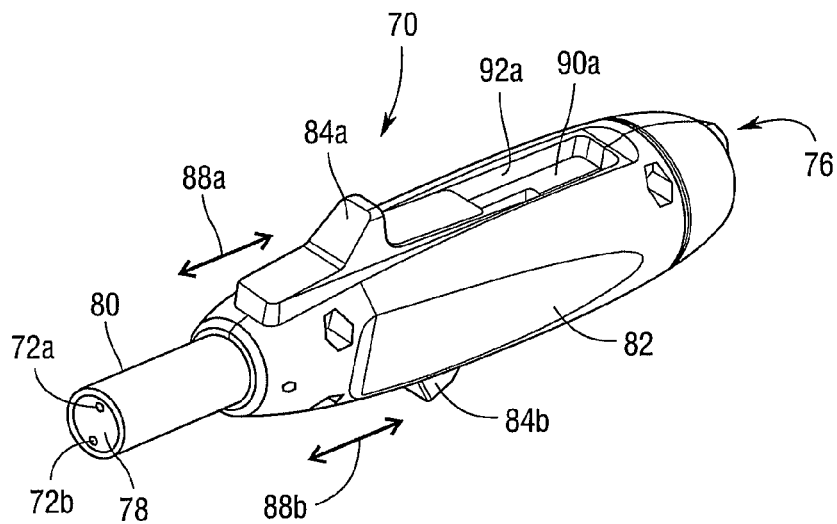
Figure 7:
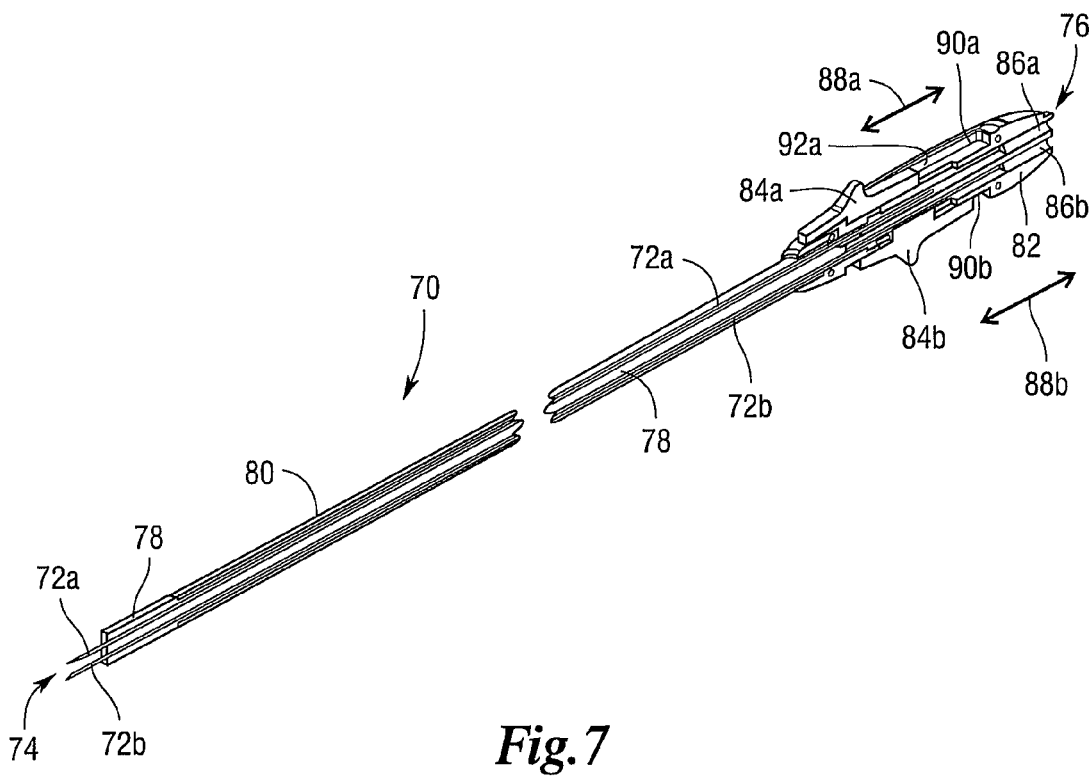
Figure 8:
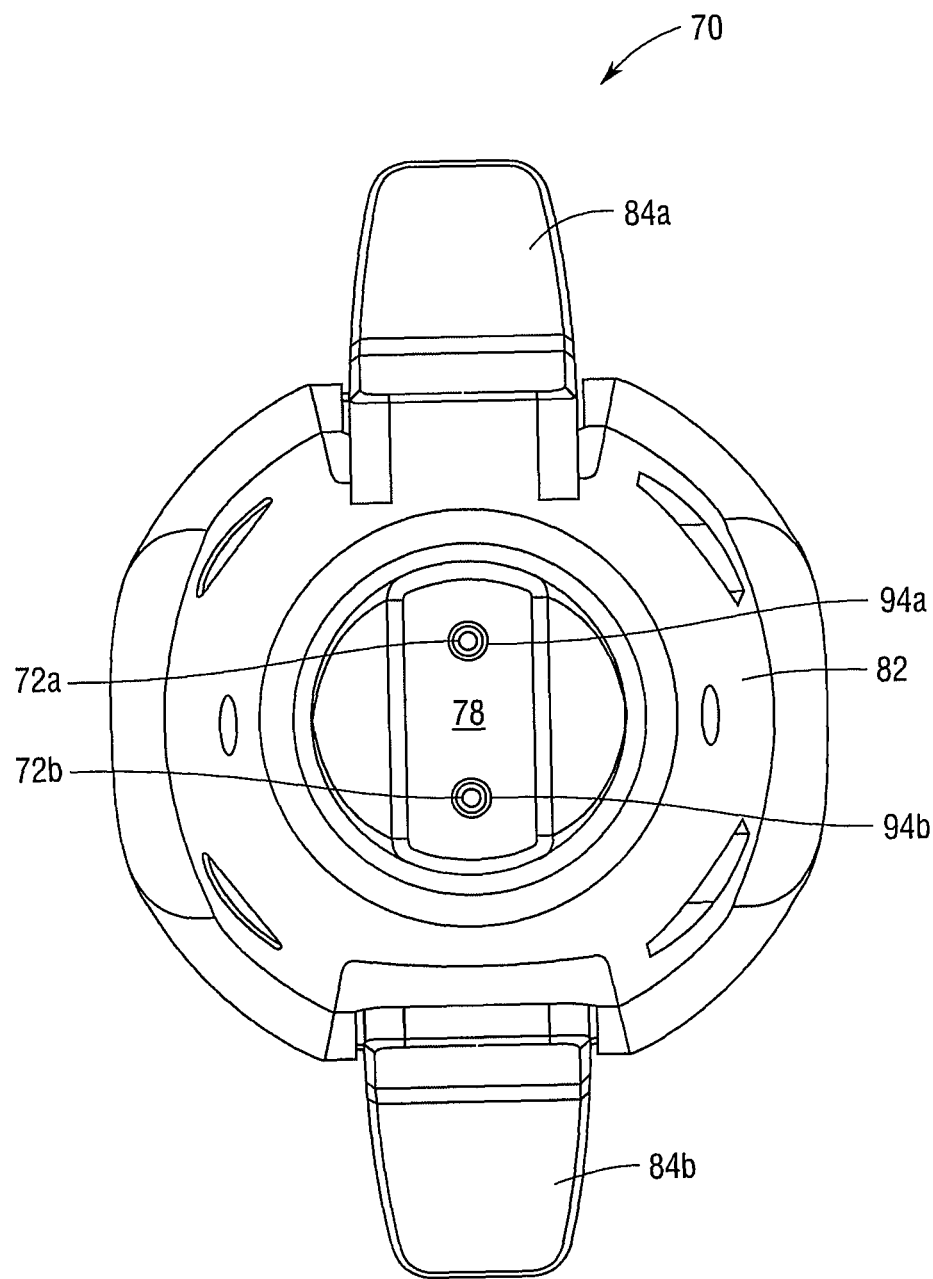
Figure 9:
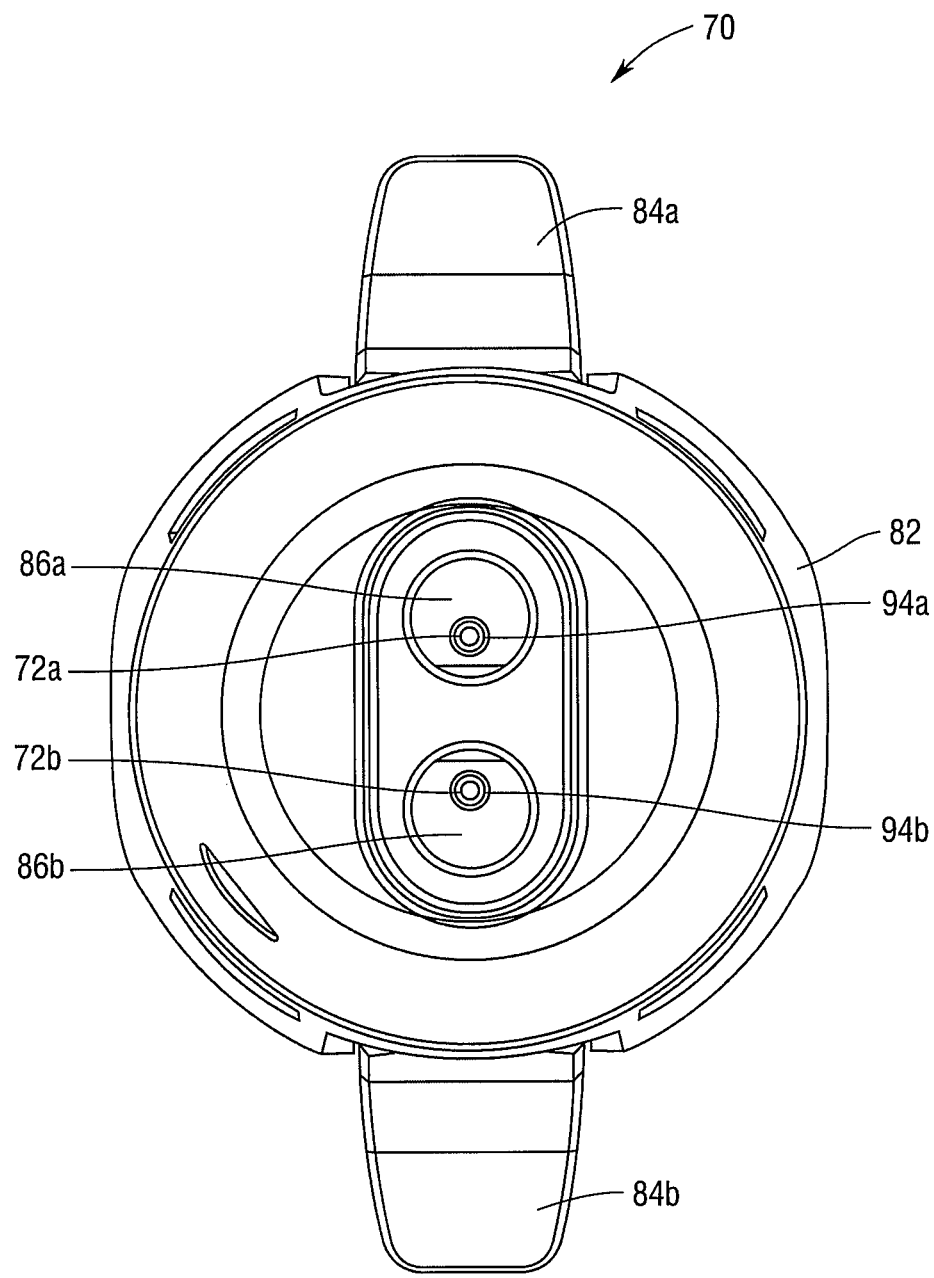
Figure 10:
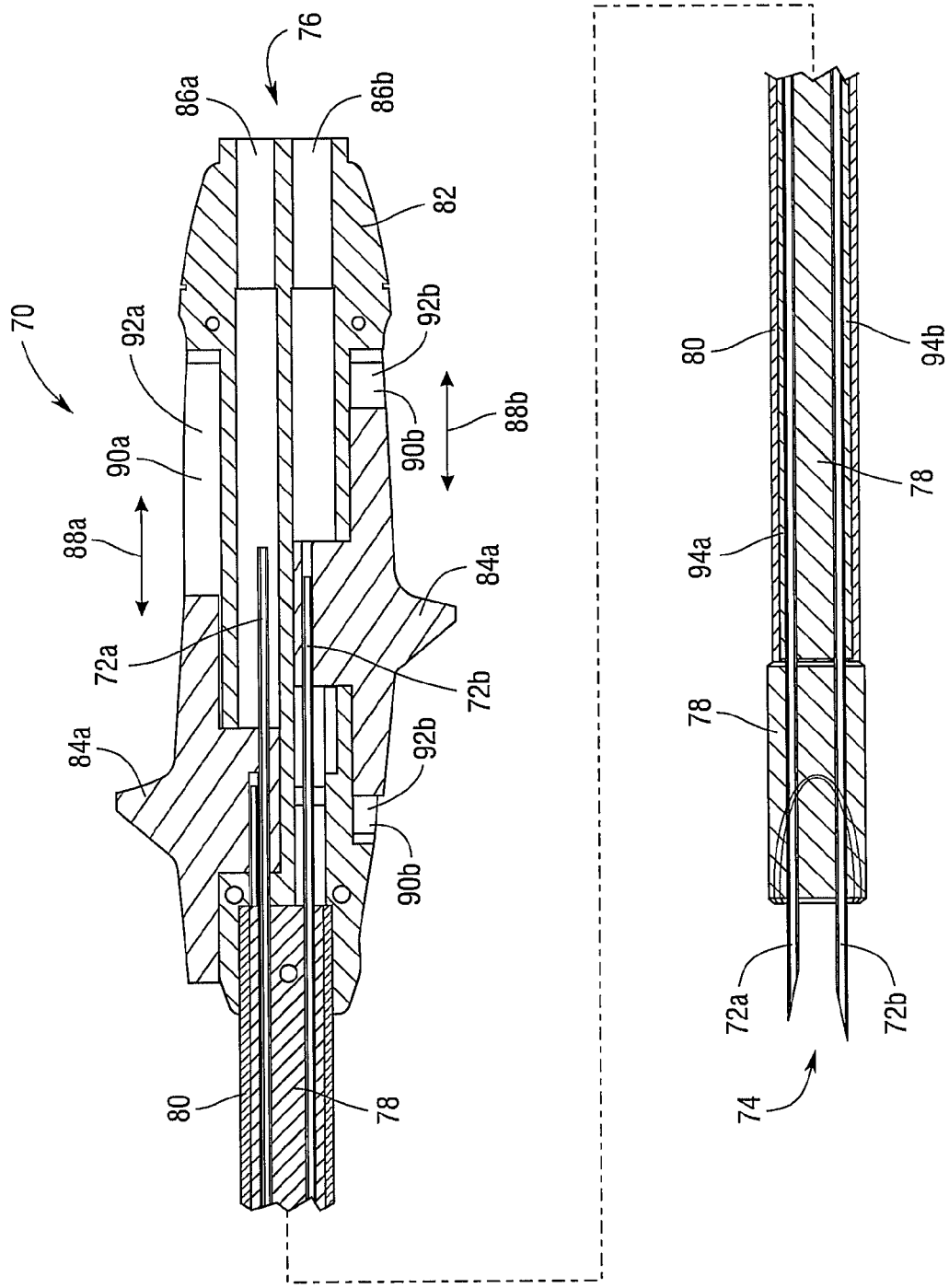

FIGS. 4-10 illustrate one embodiment of an electrical ablation device 70. FIG. 4 is a perspective side view of one embodiment of the electrical ablation device 70. FIG. 5 is a side view of one embodiment of the electrical ablation device 70. FIG. 6 is a cross-sectional perspective view of one embodiment of the electrical ablation device 70 taken across line 6-6 in FIG. 4. FIG. 7 is a cross-sectional perspective view of one embodiment of the electrical ablation device 70 taken across line 7-7 in FIG. 4. FIG. 8 is a front view of one embodiment of the electrical ablation device 70 taken along line 8-8 in FIG. 5. FIG. 9 is a back view of the electrical ablation device 70 taken along line 9-9 in FIG. 5. FIG. 10 is a cross-sectional view of one embodiment of the electrical ablation device 70 taken along the longitudinal axis.

In one embodiment, the electrical ablation device 70 may be employed to treat diseased tissue at a target tissue site in a patient. The embodiment illustrated in FIGS. 4-10 may be adapted to treat colorectal cancer (e.g., colon cancer) using electrical fields such as, for example, IRE, although the embodiments are not limited in this context as the electrical ablation device 70 can be adapted and/or configured to treat a variety of diseased tissues in the esophagus, liver, breast, brain, lung, and other organs employing a variety of electrical energy fields and waveforms. Colorectal cancer, also called colon cancer or bowel cancer, includes cancerous growths in the colon, rectum, and appendix. It is the third most common form of cancer and the second leading cause of death among cancers in the western world. Many colorectal cancers are thought to arise from adenomatous polyps in the colon. These mushroom-like growths are usually benign, but some may develop into cancer over time. The majority of the time, the diagnosis of localized colon cancer is through colonoscopy. Therapy is usually through surgery, which in many cases is followed by chemotherapy. It would be desirable to have a substantially simple and effective technique to destroy cancerous tissue in the colon. As previously described, any suitable electrical energy fields or waveforms such as IRE techniques, for example, may be employed to effectively destroy cancerous tissue cells. As previously discussed, in one embodiment, the polarity of the electrical pulses may be inverted or reversed by the electrical waveform generator 14 during the treatment process.

With reference now to FIGS. 4-10, the electrical ablation device 70 comprises an elongated flexible shaft 78 that houses two needle electrodes 72a,b. The needle electrodes 72a,b are free to extend past the distal end 74 of the electrical ablation device 70. In one embodiment, the first and second needle electrodes 72a,b are adapted to receive an electrical field such as an IRE waveform, for example, from an IRE generator. In another embodiment, the first and second needle electrodes 72a,b are adapted to receive an RF waveform from an RF generator. In one embodiment, the first and second needle electrodes 72a,b are connected to the respective positive and negative outputs of a high-voltage DC generator (e.g., the electrical waveform generator 14) at the proximal end 76. The needle electrodes 72a,b supply high voltage DC pulses to the tissue treatment region to destroy the cancerous cells located at the target site. Electrical conductors carrying the high voltage DC pulses from the electrical waveform generator 14 (FIG. 1) may be coupled to the needle electrodes 72a,b through openings 86a,b forming electrical receptacles at the proximal end 76 to receive conductive elements coupled to the electrical waveform generator 14. As previously discussed, in one embodiment, the polarity of the electrical pulses may be inverted or reversed by the electrical waveform generator 14 during the treatment process.

The electrical ablation device 70 may be employed in a method of treating cancerous tissue without destroying red blood cells. Red blood cells (erythrocytes) are not destroyed in the same manner as bi-layer lipid cells (cancerous cells). In one embodiment, the electrical ablation device 70 may be introduced through an existing endoscope, such as the endoscope 12 shown in FIG. 1. The cancerous tissue region may be visually located with the endoscope 12, and therapy may be applied by extending the needle electrodes 72a,b into the diseased tissue and energizing the needle electrodes 72a,b. Typically, 20 to 40 pulses of approximately 500-700 volts DC at approximately 100-400 µs duration each are sufficient to destroy cancerous tissues.

The flexible shaft 78 comprises first and second lumen 94a,b formed therein to slidably receive the respective first and second needle electrodes 72a,b. A flexible sheath 80 extends longitudinally from a handle portion 82 to the distal end 74. The handle portion 82 comprises a first slide member 84a and a second slide member 84b. The slider members 84a,b are received in respective slots 90a and 90b (FIG. 7) defining respective wall 92a,b. The slider members 84a,b are coupled to the respective first and second needle electrodes 72a,b. The first slide member 84a is movable in direction 88a and the second slider is movable in direction 88b. Accordingly, moving the first slide member 84a in direction 88a toward the proximal end 76 retracts the first needle electrode 72a into the flexible shaft 78. Similarly, moving the second slide member 84b in direction 88b toward the proximal end 76 retracts the second needle electrode 72b into the flexible shaft 78. The first and second needle electrodes 72a,b are independently movable by way of the respective first and second slider members 84a,b. To deploy the first and second needle electrodes 72a,b, the respective first and second slider members 84a,b can be moved independently in respective directions 88a,b toward the distal end 74.

Figure 11:
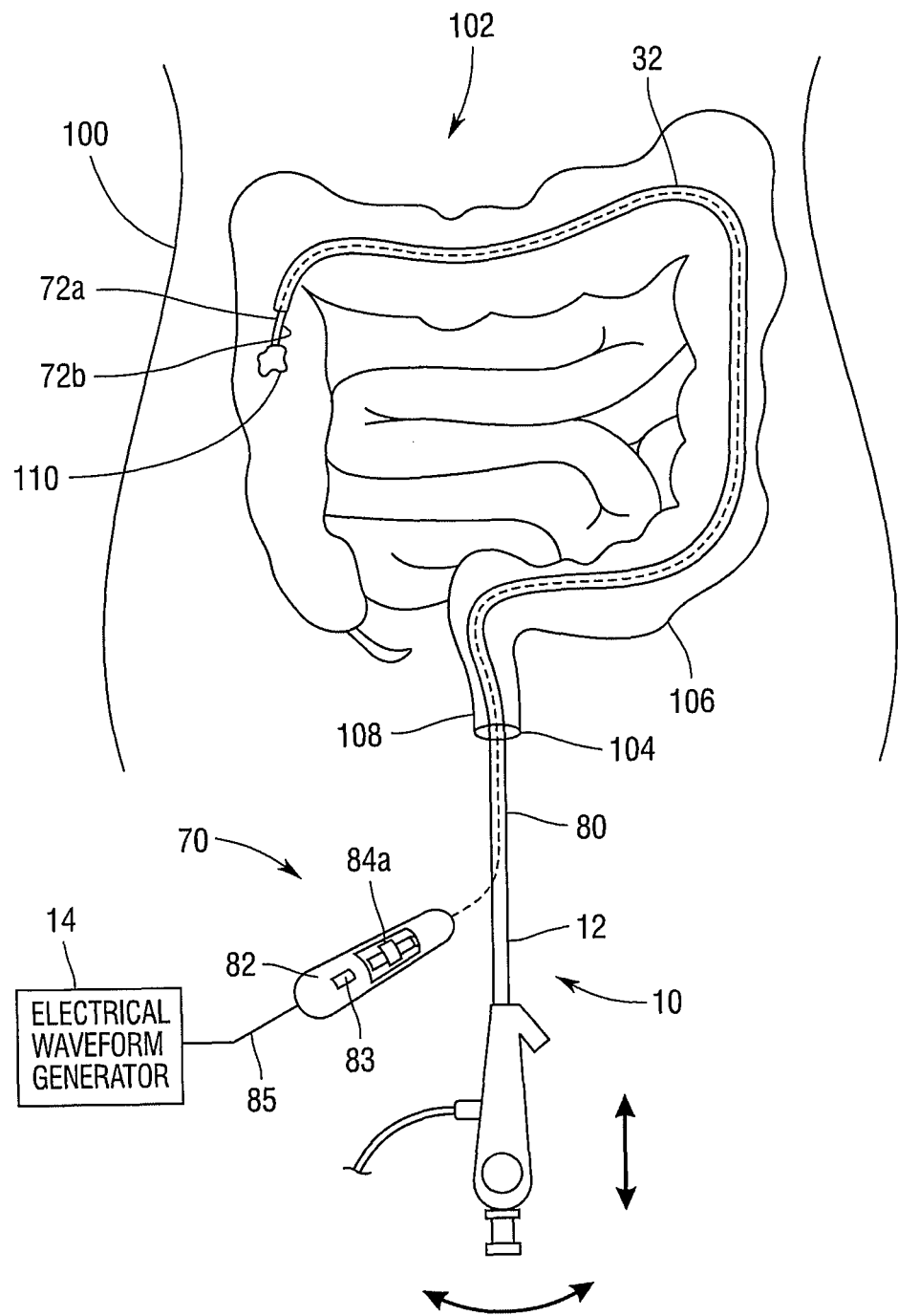
FIG. 11 illustrates the use of one embodiment of the electrical ablation system shown in FIGS. 4-10.

FIG. 11 illustrates the use of one embodiment of the electrical ablation system 70 shown in FIGS. 4-10. The electrical ablation device 70 is inserted into a hollow body or natural opening of a patient 100. The electrical ablation device 70 is introduced to diseased tissue 110 through the colon 102. The electrical ablation device 70 is inserted into the colon 102 through the anus 104. The colon 102 includes a sphincter muscle 106 disposed between the anus 104 and the rectum 108. The electrical ablation system 70 is steerable and maneuverable and may be steered or maneuvered through several turns through the colon 102.

The electrical ablation system 70 may be introduced endoscopically through the endoscope 12. The operator inserts the flexible shaft 32 of the endoscope 12 into the anus 104 and maneuvers it through the colon 102. The operator uses endoscopic visualization through the viewing port of the endoscope 12 to position the distal end 74 of the electrical ablation device 70 at the target site of the diseased tissue 110. At the target site, the first and second needle electrodes 72a,b are inserted into the diseased tissue 110 such that they are placed in intimate contact with the diseased tissue 110 to be treated within the field of view of the flexible endoscope 12. Watching through the viewing port of the endoscope 12, the operator can actuate a switch 83 located on the handle 82 to electrically connect the electrodes 72a,b to the waveform generator 14 through a corresponding set of conductors 85 inserted through the electrical receptacle openings 86a,b. Electric current then passes through the portion of the diseased tissue 110 positioned between the electrodes 72a,b. When the operator observes that the tissue within the field of view has been sufficiently ablated, the operator deactuates the switch 83 to stop the ablation. The operator may reposition either of the endoscopic electrodes 72a for subsequent tissue treatment, or may withdraw the electrical ablation device 70 (together with the flexible endoscope 12). As previously discussed above with reference to FIGS. 1 and 2A-D, in the embodiment described in FIGS. 4-11, either one or both of the electrodes 72a,b may be retracted with one of the electrodes acting as a pivot while the other electrode is repositioned to enable the operator to cover a larger area of the tissue treatment region.

If the diseased tissue 110 is located on the liver, the distal end of the endoscope 12 can be advanced into the sigmoid colon. Once in the sigmoid colon, an instrument such as a needle knife can be advanced through the lumen of the endoscope 12. The needle knife can then cut an opening through the sigmoid colon and into the peritoneal space (under visualization). The endoscope 12 can then be advanced into the peritoneal space and manipulated until the liver is in view. This can be done under visualization using the view from the endoscope 12 or with fluoroscopy. The electrical ablation device 70 and the first and second electrodes 72a,b are then advanced into the liver to the target site.

Figure 12:
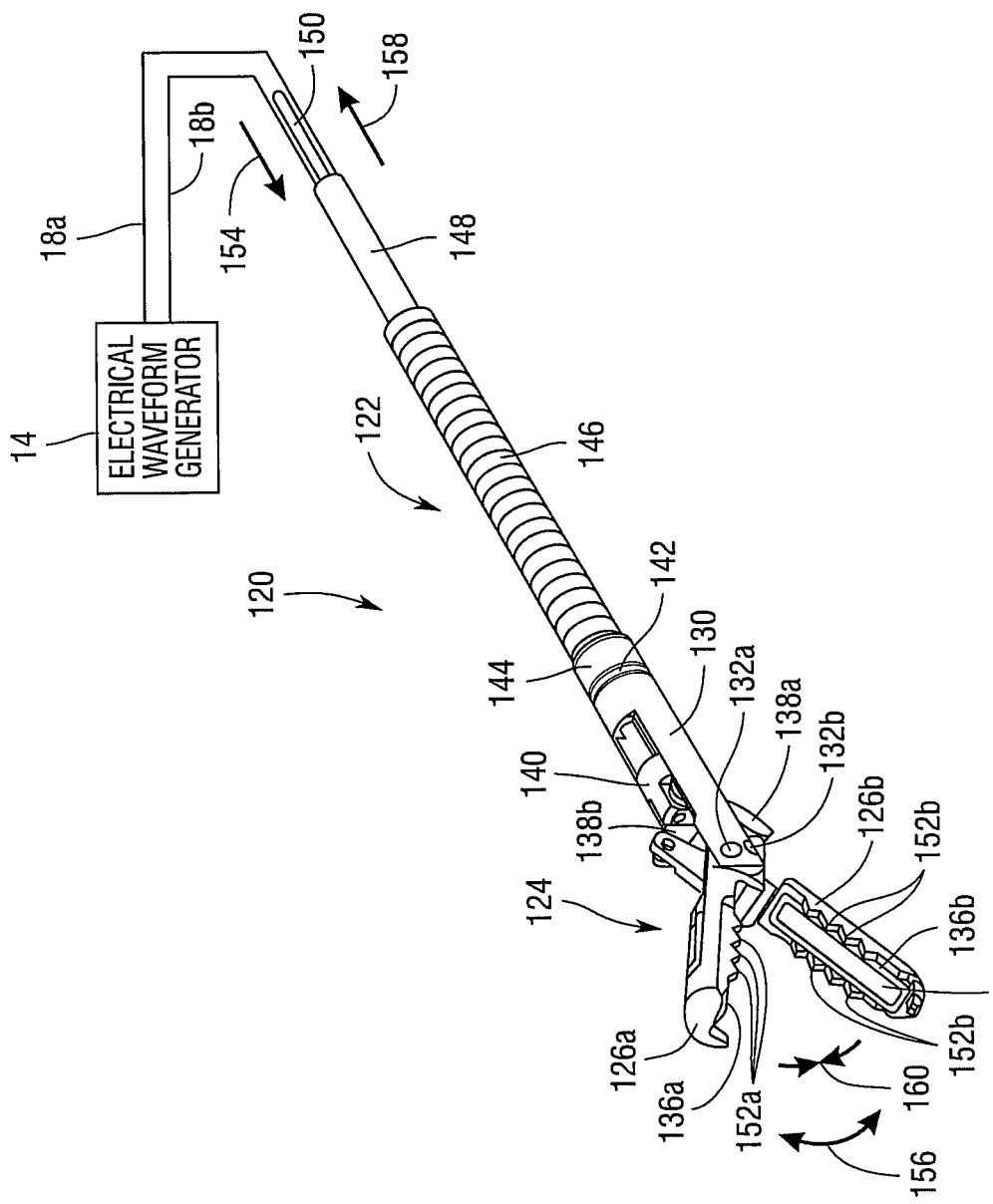
FIGS. 12-18 illustrate one embodiment of an electrical ablation device.
Figure 13:
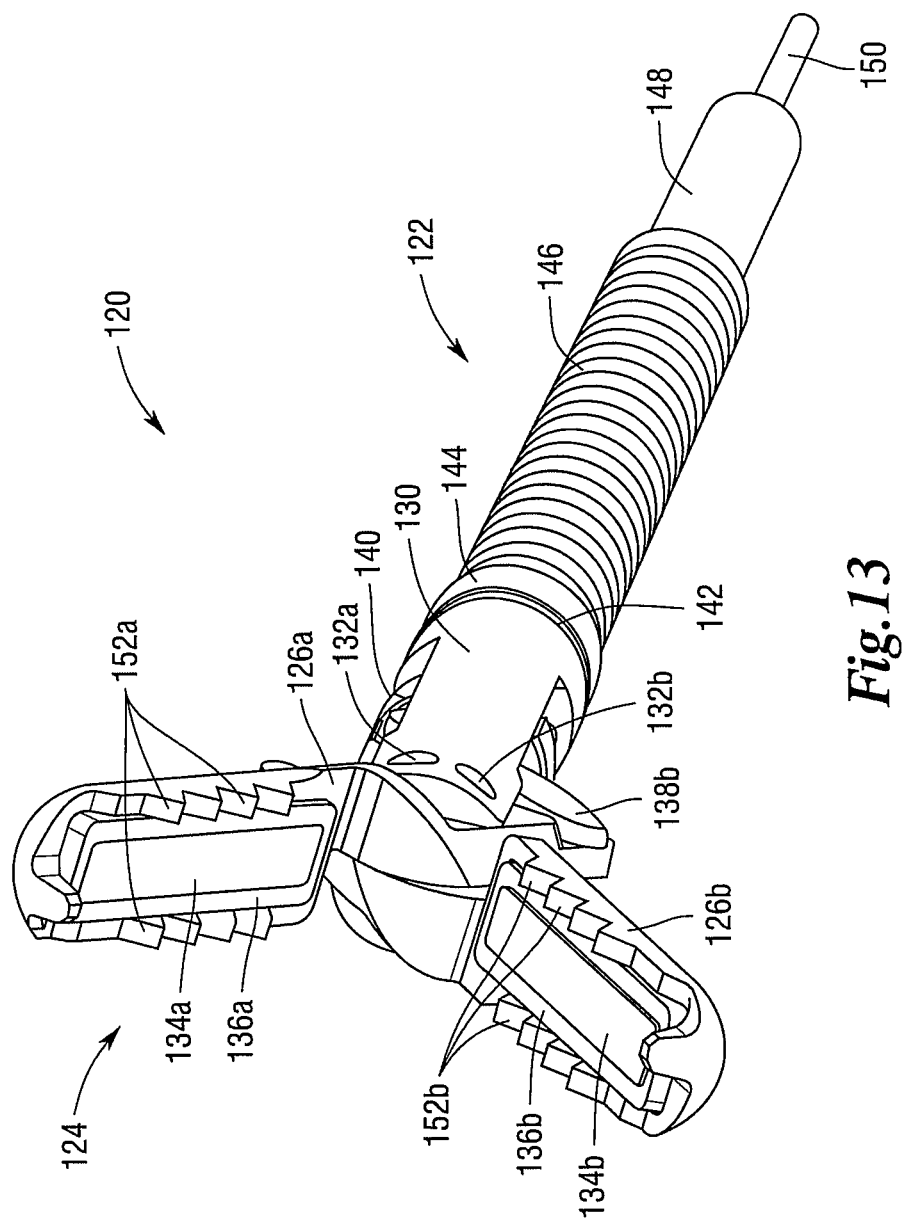
Figure 14:
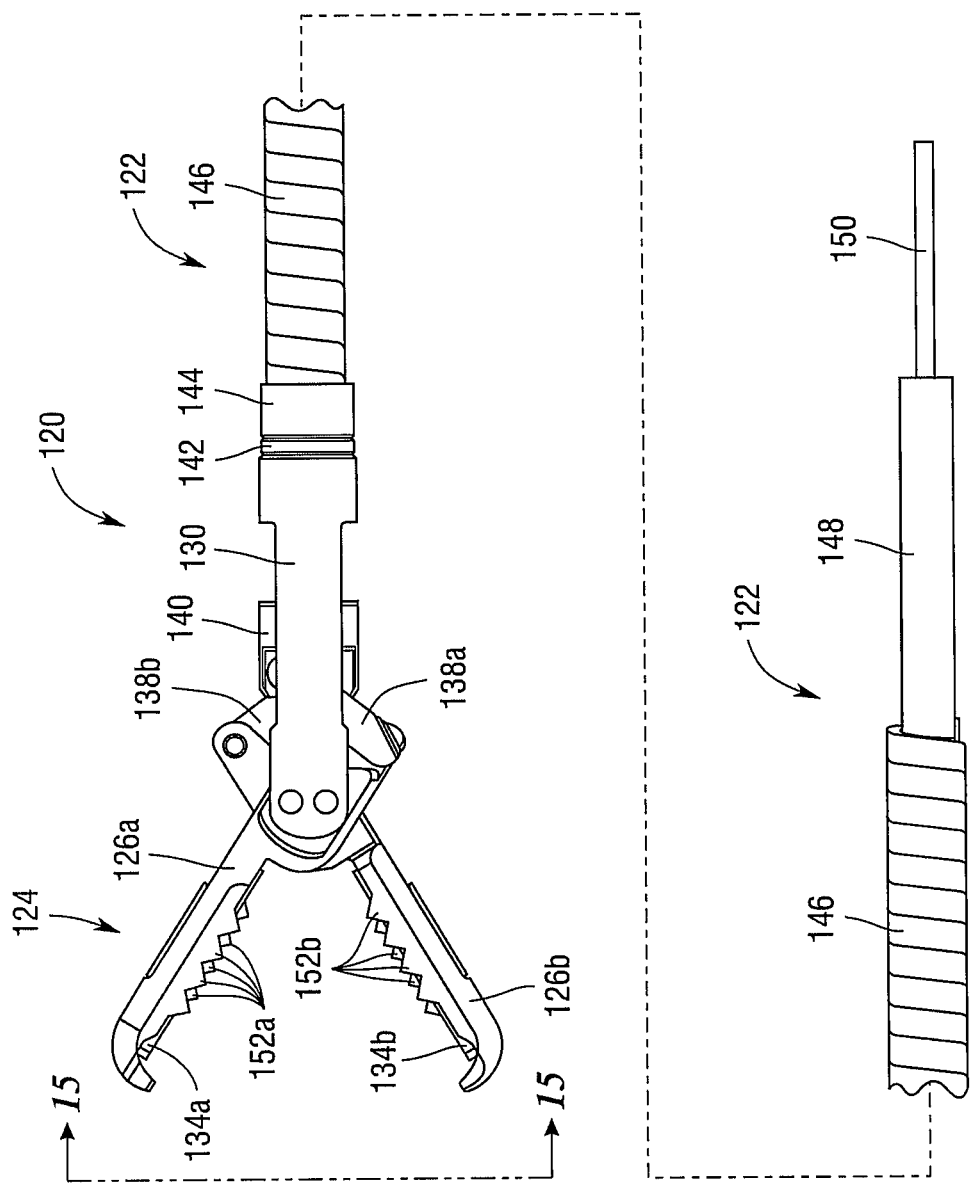
Figure 15:
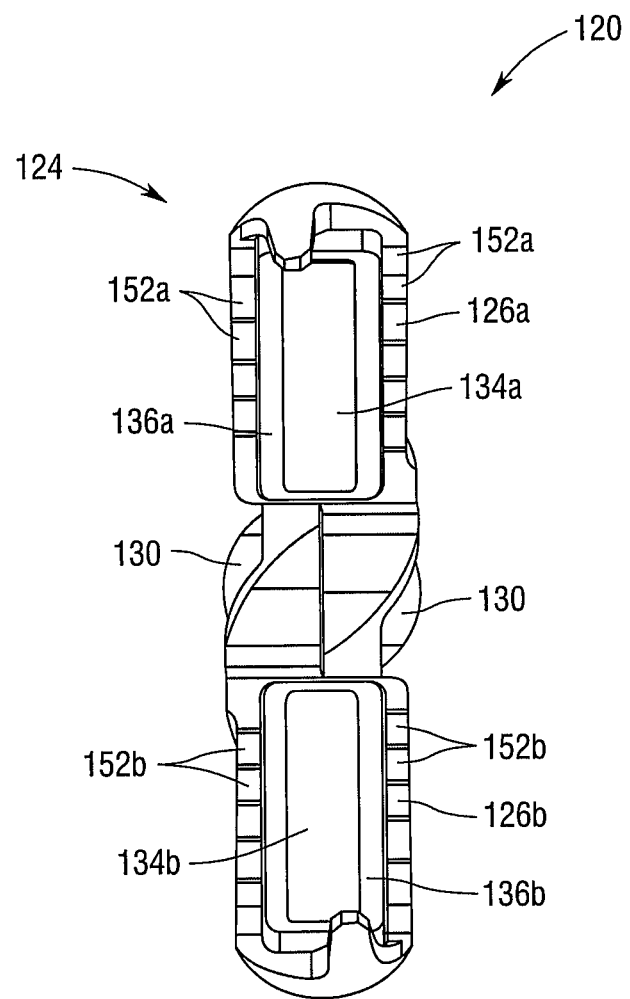
Figure 16:
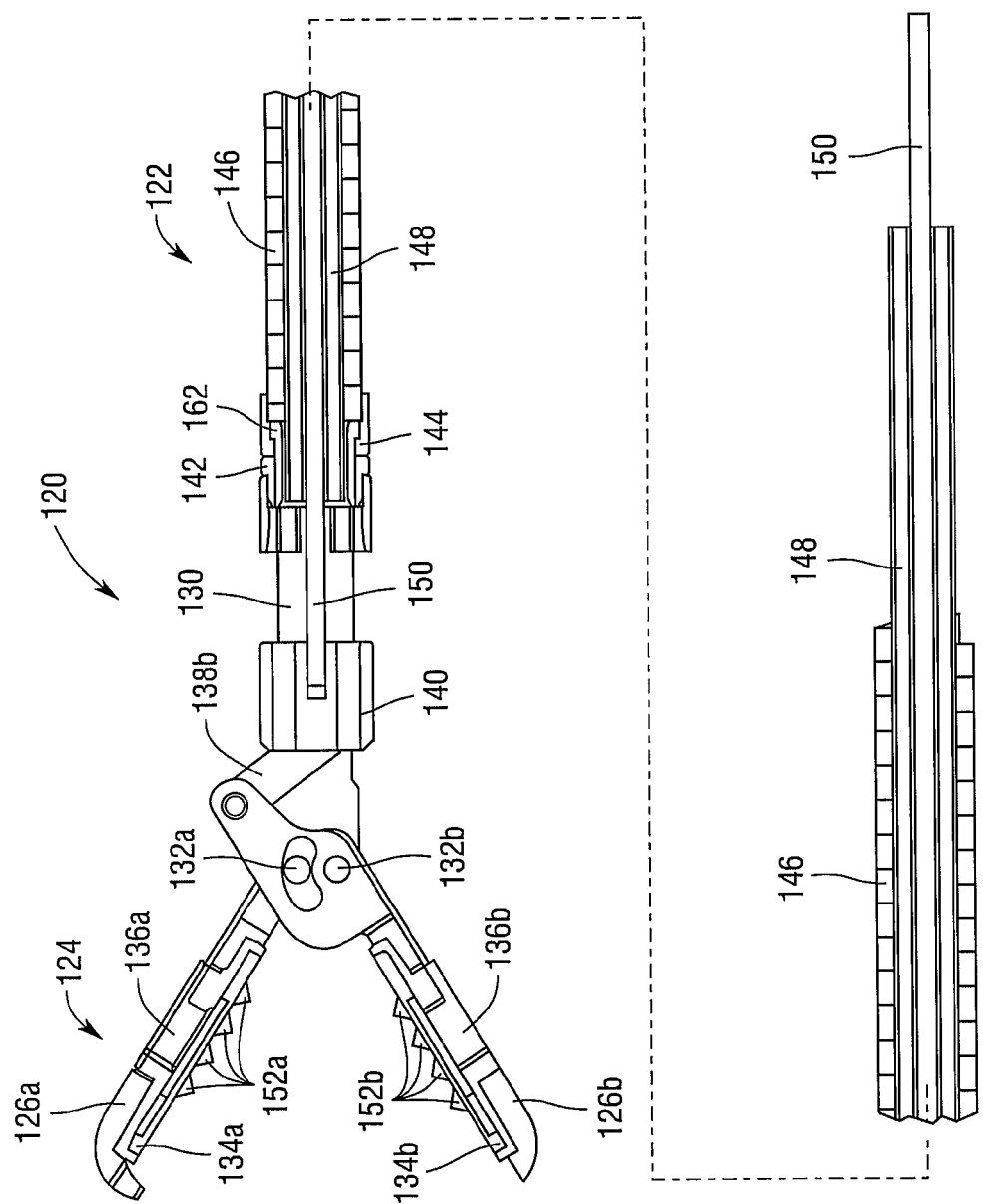
Figure 17:
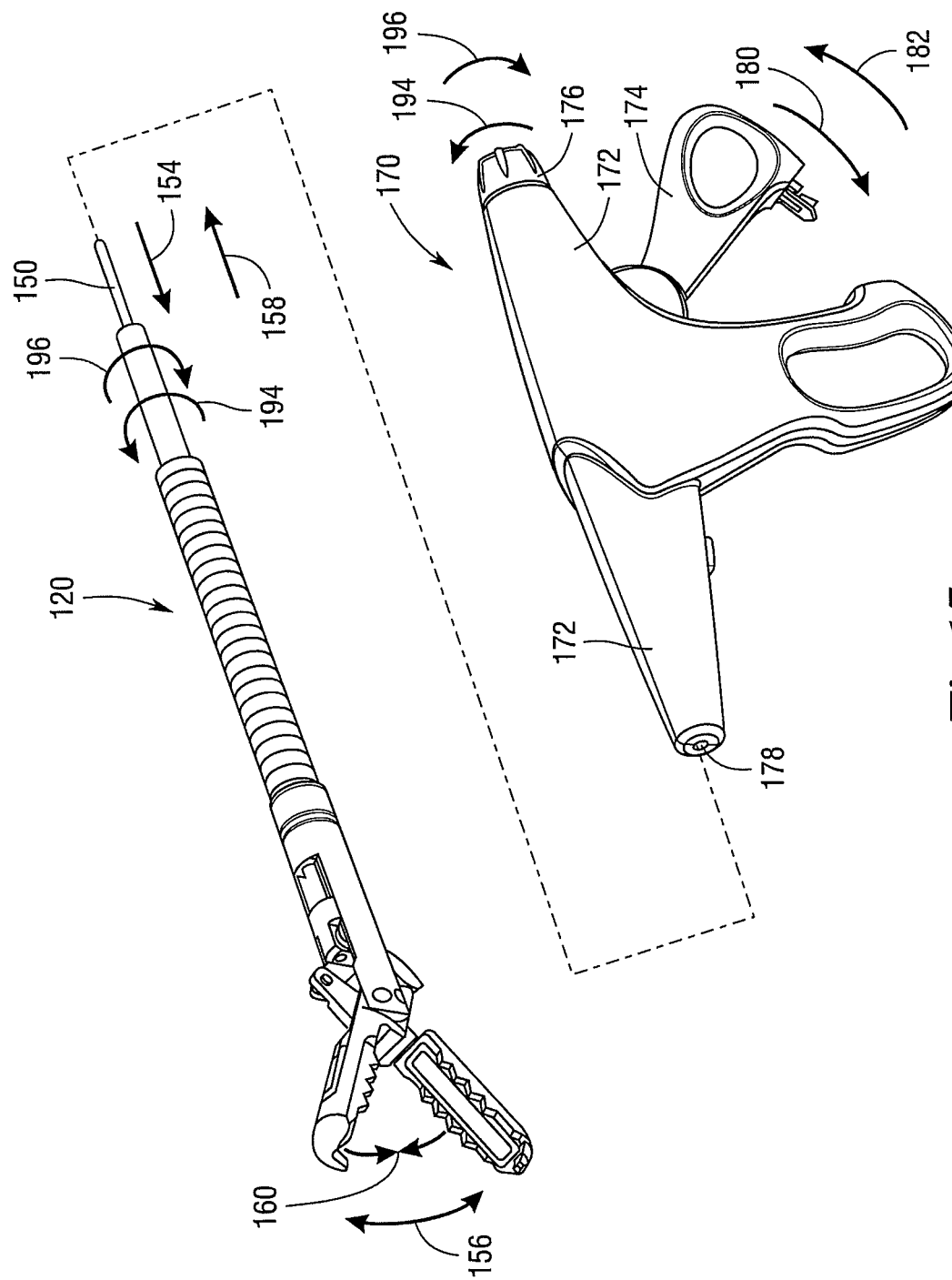
Figure 18:
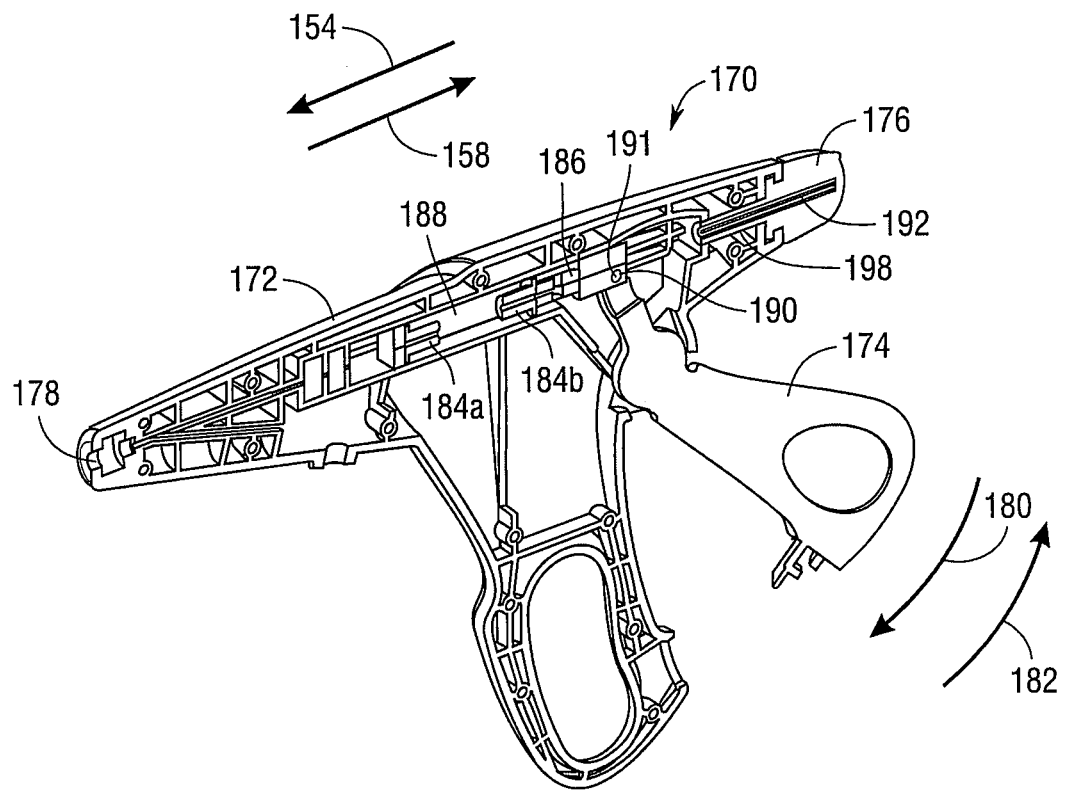

FIGS. 12-18 illustrate one embodiment of an electrical ablation device 120. FIG. 12 is a top side perspective side view of the electrical ablation device 120. FIG. 13 is a bottom side perspective view of one embodiment of the electrical ablation device 120. FIG. 14 is a side view of one embodiment of the electrical ablation device 120. FIG. 15 is a front view of one embodiment of the electrical ablation device taken along line 15-15 in FIG. 14. FIG. 16 is a cross-sectional view of one embodiment of the electrical ablation device 120 taken along the longitudinal axis. FIG. 17 is a perspective view of one embodiment of the electrical ablation device and a handle assembly coupled to thereto. FIG. 18 is a cross-sectional view of one embodiment of the right-hand portion of the handle assembly.

With reference now to FIGS. 12-16, the electrical ablation device 120 comprises an elongated flexible portion 122 and a clamp jaw portion 124. The clamp jaw portion 124 comprises a first jaw member 126a and a second jaw member 126b. The first and second jaw members 126a,b are pivotally coupled to a clevis 130 by respective first and second clevis pins 132a,b. The first jaw member 126a comprises an electrode portion 134a and an electrical insulator portion 136a. The first jaw member 126a also comprises a plurality of serrations 152a or teeth. The second jaw member 126b comprises an electrode portion 134b and an electrical insulator portion 136b. The second jaw member 126b also comprises a plurality of serrations 152b or teeth. The first jaw member 126a is coupled to an actuator 140 by a first link 138a. The second jaw member 126b is coupled to the actuator 140 by a second link 138b.

The elongated portion 122 comprises an elongated flexible member 146 coupled to the clevis 130 by a bushing coupler 142 and a ring capture 144. In one embodiment, the elongated flexible member 146 comprises a flat spring coil pipe. An inner housing coupler 162 (FIG. 16) is coupled to the ring capture 144 and the bushing coupler 142. A multi-lumen elongated flexible member 148 is disposed within the elongated flexible member 146. An elongated actuator member 150 is provided within one of the lumens formed within the multi-lumen elongated flexible member 148. The elongated actuator member 150 may be formed as a solid rod or a tube. The elongated actuator member 150 is coupled to the actuator 140. The elongated actuator member 150 moves reciprocally in the directions indicated by arrows 154 and 158. When the elongated actuator member 150 is moved in the direction indicated by arrow 154, the first and second jaw members 126a,b open in the direction indicated by arrow 156. When the elongated actuator member 150 is moved in the direction indicated by arrow 158, the first and second jaw members 126a,b close in the direction indicated by arrow 160. Accordingly, the first and second jaw members 126a,b cooperate and act like forceps or tongs to grasp and contain tissue, such as dysplastic or cancerous mucosal tissue, for example, between the serrations 152a,b.

First and second electrical conductors 118a,b are electrically coupled to the respective first and second electrodes 134a,b formed in the respective first and second jaw members 126a,b. In one embodiment, the first and second electrodes 134a,b may be formed having a substantially flat paddle-like shape. The first and second electrical conductors 118a,b are received through lumens formed in the multi-lumen elongated flexible member 148 and are coupled to the first and second electrodes 134a,b in any suitable manner. A switch may be coupled to the electrical conductors 118a,b to enable an operator to activate and deactivate the first and second electrodes 134a,b after tissue at the desired target site is grasped between the first and second jaw members 126a,b.

In one embodiment, the electrical ablation device 120 may be employed to treat diseased tissue at a target tissue site in a patient. The embodiment illustrated in FIGS. 12-16 may be adapted to treat various types of diseased tissue such as dysplastic or cancerous mucosal tissue that can be found in the body. When such diseased mucosal tissue is discovered, it may be biopsied and observed over time. Although the diseased mucosal tissue may be removed or treated with a thermal device to destroy the tissue, removing the diseased mucosal tissue or destroying it in this manner can damage the thin wall thickness of the particular organ (such as esophagus or stomach) adjacent to the mucosal tissue to the extent that a perforation can occur in the organ. The embodiment of the electrical ablation device 120 shown in FIGS. 12-16 comprise a forceps or paddle-like device comprising the first and second jaw members 126*a,b* operatively coupled to the actuator 140 and the elongated actuator member 150 to grasp and contain the mucosal tissue between the first and second electrodes 134*a,b*. Once the tissue is grasped or engaged by the serrations 152*a,b* formed in the first and second jaw members 126*a,b* and contained between the first and second electrodes 134*a,b*, electrical energy may be applied to the first and second electrodes 134*a,b* to destroy the tissue contained therebetween. The first and second electrodes 134*a,b* comprise electrically conductive surfaces adapted to receive an electrical field from a suitable waveform generator. In one embodiment, the first and second electrodes 134*a,b* are adapted to receive an electrical field such as an IRE waveform from a suitable IRE waveform generator. In another embodiment, the first and second electrodes 134*a,b* are adapted to receive a RF waveform from a suitable RF waveform generator. In one embodiment, the first and second electrodes 134*a,b* are connected to the electrical waveform generator 14 such as a high voltage DC waveform generator (±500 VDC), for example. It has been shown that when high electric fields are applied to tissue, the cell membrane will form an aqueous pathway through which molecules can flow (electroporation). If the electric field is increased to a sufficient level, the wall of the cell will rupture and subsequent apoptosis/necrosis will occur (irreversible electroporation). This occurs on the order of 1 millisecond, therefore very little energy is put into the tissue and very little heating occurs. Therefore, the tissue can be treated more precisely and safely with the electrical ablation device 120 than complete removal or thermal destruction of the diseased mucosal tissue. As previously discussed, in one embodiment, the polarity of the electrical pulses may be inverted or reversed by the electrical waveform generator 14 during the treatment process. Electrical waveform generators are discussed in commonly owned U.S. patent applications titled "Electroporation Apparatus, System, and Method," Ser. No. 11/706,591 to Long and "Electroporation Ablation Apparatus, System, and Method," Ser. No. 11/706,766 to Long, both of which are incorporated herein by reference.

FIG. 17 is a perspective view of the electrical ablation device 120 and a handle assembly 170 coupled to thereto. The handle assembly 170 comprises a base handle portion 172, a trigger 174, a rotation knob 176, and an opening 178 to receive the distal end of the elongated actuator member 150. The trigger 174 is operatively coupled to the elongated actuator member 150. When the trigger 174 is pivotally moved (e.g., squeezed) in the direction indicated by arrow 180, the elongated actuator member 150 moves in the direction indicated by arrow 158, and the first and second jaw members 126*a,b* close in the direction indicated by arrow 160. When the trigger 174 is pivotally moved (e.g., released) in the direction indicated by arrow 182, the elongated actuator member 150 moves in the direction indicated by arrow 154, and the first and second jaw members 126*a,b* open in the direction indicated by arrow 156. The distal end of the elongated actuator member 150 is received within a neck portion 198 (FIG. 18) of the rotation knob 176. When the rotation knob 176 is rotated in the direction indicated by arrow 194, the electrical ablation device 120 is also rotated in the direction indicated by arrow 194. When the rotation knob 176 is rotated in the direction indicated by arrow 196, the electrical ablation device 120 is also rotated in the direction indicated by arrow 196.

FIG. 18 is a sectional view of the right-hand portion of the handle assembly 170. The distal end of the elongated actuator member 150 is received in the opening 178. The distal end of the elongated actuator member 150 is fixedly received in the first and second force limit spring holders 184*a,b*, shaft collar 186, and a slot 192 or groove formed in the neck portion 198 of the rotation knob 176. The trigger 174 is coupled to a force limit slider 188 at a pivot point 190 by a pivot pin 191. Accordingly, when the trigger 174 is squeezed in direction 180, the force limit slider 188 slides in the direction indicated by arrow 158 and a portion of the distal end of the elongated actuator member 150 is slidably received within the neck portion 198 of the rotation knob 176. When the trigger 174 is released, the force limit slider 188 moves in the direction indicated by arrow 154 by the spring force stored in the spring.

FIG. 19 illustrates one embodiment of an electrical ablation device 200. FIG. 20 is an end view of the electrical ablation device 200 taken along line 20-20. The electrical ablation device 200 can be employed to treat cancerous cells in a circulatory system of a patient. Cancerous cells can become free and circulate in the circulatory system as well as the lymphomic system. These cells can form metastasis in organs such as the liver. In one embodiment, the electrical ablation device 200 employs an electrical field suitable to destroy tissue cells at the treatment site. The electrical ablation device 200 comprises a tubular member 204 defining a central opening 203 for receiving blood therethrough. In one embodiment, the tubular member 204 may be a small, expandable tube used for inserting in a vessel or other part, similar to a stent. The tubular member 204 may be temporarily implanted in the vessel for electrical ablation treatment of blood flowing therethrough. In another embodiment, the tubular member 204 may be located externally to the patient to receive blood from a blood vessel and to return the blood to a blood vessel. Blood received from the patient is treated. After treatment, the blood is circulated back to the patient through a blood vessel. As previously discussed, in one embodiment, the polarity of the electrical pulses may be inverted or reversed by the electrical waveform generator 14 during the treatment process.

In the embodiment illustrated in FIGS. 19 and 20, blood is received through an opening 202*a* of the tubular member 204. The tubular member 204 comprises a small, expandable body 206 that defines a central opening 203 and may be inserted into a vessel or other body part via a slender thread, rod, or catheter. The tubular member 204 comprises a first positive electrode 208*a* and a second negative electrode 208*b*. The first and second electrodes 208*a,b* are coupled to the electrical waveform generator 14 (FIG. 1) via respective electrical conductors 209*a,b*. The first and second electrodes 208*a,b* may be located on opposite portions of the tubular member 204. In one embodiment, the first and second electrodes 208*a,b* are adapted to receive an IRE waveform from an IRE generator. In another embodiment, the first and second electrodes 208*a,b* are adapted to receive a RF waveform from an RF generator. In one embodiment, the electrical ablation device 200 employs IRE to destroy the cancerous cells without destroying healthy blood cells. IRE has been shown to be an effective way to destroy the cancerous cells. An IRE electric field is created between the first and second electrodes 208*a,b* when they are energized by the electrical waveform generator 14. The first and second electrodes 208*a,b* are adapted to receive high voltage DC pulses from the waveform generator 14 to destroy the cancerous cells in the bloodstream or other flowable substance passing through the tubular member 204. If the pulse width of the voltage is reduced to a sufficiently short length (t<60 nanoseconds) and the voltage is increased (V>10 kV/cm), then the contents (organelles) of the cancerous cells will be altered in a way that will cause the cell to become necrotic (apoptosis) yet the plasma membrane (cell wall) will not be affected. Likewise, the plasma membrane of the red blood cell will be preserved, and because red blood cells do not contain organelles similar to cancerous cells, they will not be destroyed.

FIG. 21 illustrates one embodiment of the electrical ablation device 200 implanted in a blood vessel 210 of a patient. The stent-like tubular member 204 may be implanted internally within the patient. The stent-like tubular member 204 may be inserted into a tubular structure, such as the blood vessel 210, to receive blood 212 through an inlet opening 202a. The blood 212 flows through the stent-like tubular member 204 in the direction indicated by arrow 205 and exits through an outlet opening 202b. When the electrodes 208a,b are energized with high voltage electrical energy such as DC pulses generated by the waveform generator 14 (FIG. 1), for example, the cancerous cells which pass through the central opening 203 are destroyed. As previously discussed, however, the red blood cells (erythrocytes) will not be destroyed if the cancerous cells are treated with electrical energy having a suitable pulse width and voltage.

FIG. 22 illustrates one embodiment of the electrical ablation device 200 located external to a patient. In another embodiment, the tubular member 204 may be located externally of the patient to circulate blood 212 therethrough to treat the cancerous cells in the blood 212 with IRE. The tubular member 204 receives the blood 212 in the inlet opening 202a from one end of a first blood vessel 214a of a patient and supplies the blood 212 to a second blood vessel 214b of the patient through an outlet opening 202b as the blood 212 flows in direction 205. As the blood 212 passes through the central opening 203, the cancerous cells are destroyed by the electrical field waveform while the normal red blood cells are unharmed.

Figure 23:
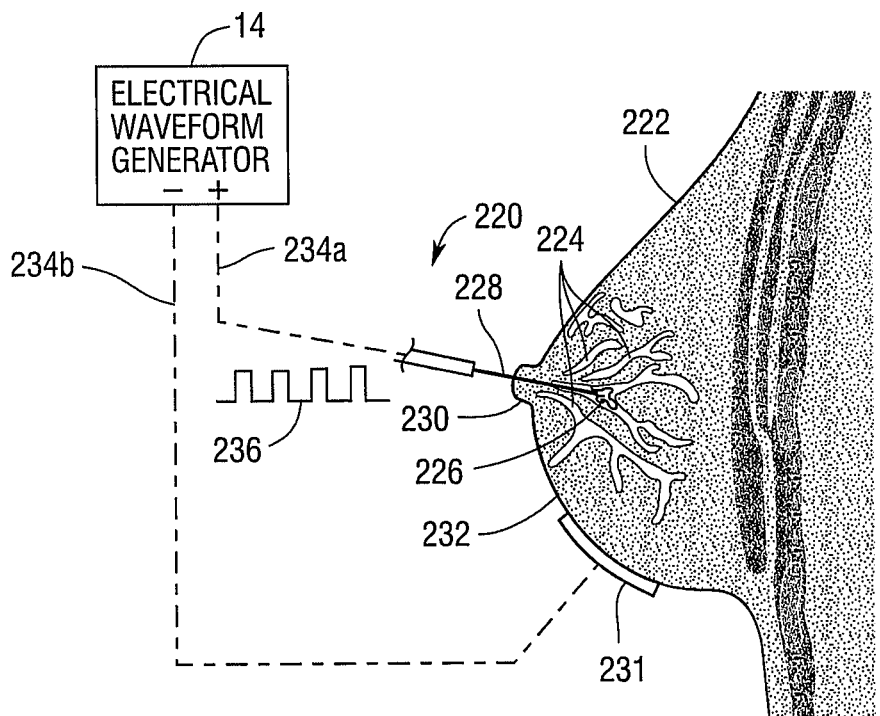
FIG. 23 illustrates one embodiment of an electrical ablation device to treat diseased tissue within a lactiferous duct of a breast by delivering electrical energy to the lactiferous duct.

FIG. 23 illustrates one embodiment of an electrical ablation device 220 to treat diseased tissue within a lactiferous duct of a breast by delivering electrical energy to the lactiferous duct. FIG. 23 illustrates a cross-sectional view of a woman's breast 222. In one embodiment, the electrical ablation device 220 may be employed to treat cancerous tissue 226 within lactiferous ducts 224 of the breast 222. Cancerous tissue 226 in the breast 222, including breast cancer tumors that are 2 cm or less, may be treated with ablation using electrical fields. These techniques destroy the cancerous tissue 226 in a less invasive manner as compared with lumpectomy or mastectomy. The electrical ablation device 220 employs electrical fields to destroy the cancerous tissue 226. As previously discussed, in one embodiment, the electrical fields may be applied to destroy tissue cells at the treatment site. In one embodiment, the electrical ablation device 220 comprises a first electrode 228 comprising an electrically conductive elongated member such as a wire or a flexible electrically conductive tube. The first electrode 228 is introduced through a nipple 230 portion of the breast 222 into one of the lactiferous ducts 224 of the breast 222 where the cancerous tissue 226 is located. The first electrode 228 may be introduced into the lactiferous duct 224 under fluoroscopy, ultrasound guidance, or other well-known techniques. A second electrode 231 comprising an electrically conductive pad is located on an exterior or outside portion 232 of the breast 222. The second electrode 231 has a much larger surface area than the first electrode 228. In one embodiment, the first and second electrodes 228, 231 are adapted to receive electrical fields in the form of an IRE waveform from an IRE generator.

In another embodiment, the first and second electrodes 228, 231 are adapted to receive electrical fields in the form of a RF waveform from an RF generator. In the illustrated embodiment, the first electrode 228 is connected to the positive output of the waveform generator 14 through a first lead 234a, and the second electrode 231 is connected to a negative output of the waveform generator 14 through a second lead 234b. As previously discussed, electrical waveform generator 14 is capable of generating high voltage pulse waveforms of various amplitude, frequency, and pulse duration. In other embodiments, the polarity of the first and second electrodes 228, 231 may be inverted. Multiple pulses may be supplied to the first electrode 228 and the pad of the second electrode 231 to destroy the cancerous tissue 226 occupying the space in the duct 224. A pulse train 236 comprising 20 to 40 pulses of ±500 to ±700 VDC of approximately 0.4 milliseconds in duration each is sufficient to destroy the cancerous tissue 226. As previously discussed, in one embodiment, the polarity of the electrical pulses may be inverted or reversed by the electrical waveform generator 14 during the treatment process.

Figure 24:
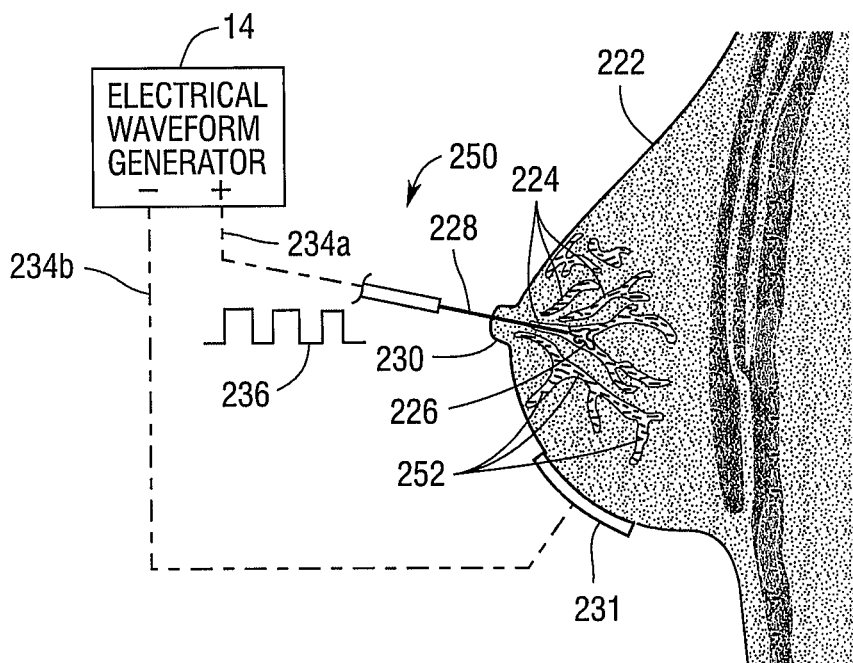
FIG. 24 illustrates one embodiment of an electrical ablation device to treat diseased tissue within a lactiferous duct of a breast by delivering electrical energy to the lactiferous duct.

FIG. 24 illustrates one embodiment of an electrical ablation device 250 to treat diseased tissue within a lactiferous duct of a breast by delivering electrical energy to the lactiferous duct. FIG. 24 illustrates a cross-sectional view of a woman's breast 222. In one embodiment, a conductive fluid 252 may be introduced into the duct 224 to extend the operating range of the first electrode 228 to treat the cancerous tissue 226 within the duct 224. As discussed above, the pulse train 236 comprising 20 to 40 pulses of ±500 to ±700 VDC of approximately 0.4 milliseconds in duration each is sufficient to destroy the cancerous tissue 226. As previously discussed, in one embodiment, the polarity of the electrical pulses may be inverted or reversed by the electrical waveform generator 14 during the treatment process.

Figure 25:
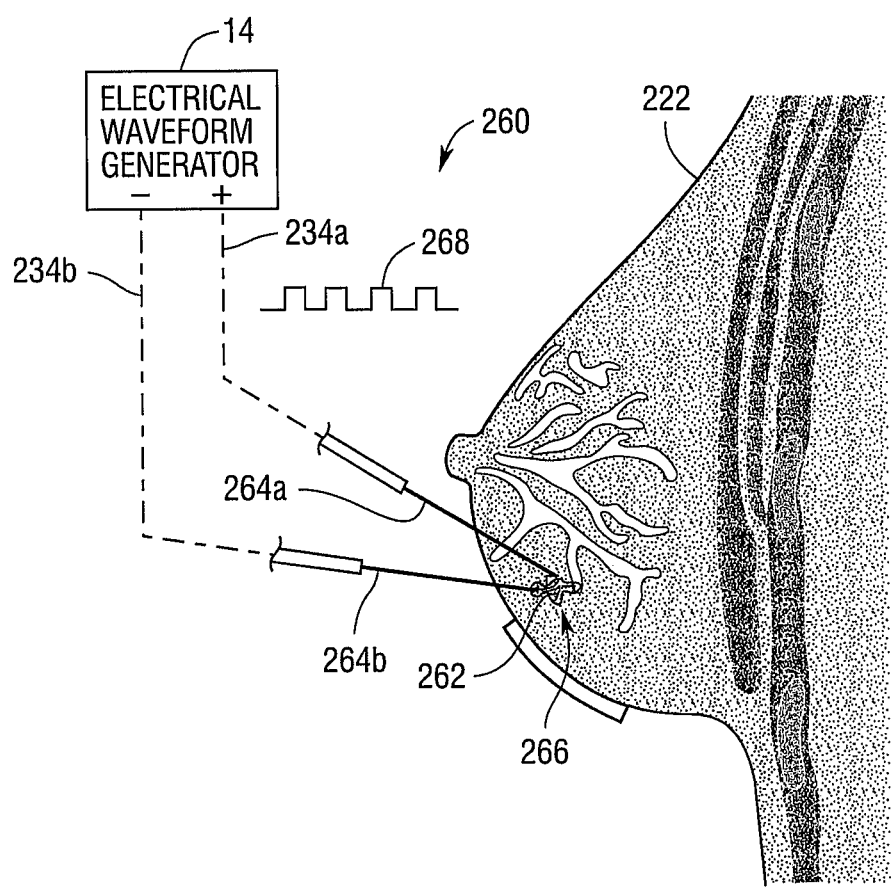
FIG. 25 illustrates one embodiment of an electrical ablation device to treat diseased tissue located outside of a lactiferous duct of a breast by delivering electrical energy to the breast outside of the lactiferous duct.

FIG. 25 illustrates one embodiment of an electrical ablation device 260 to treat diseased tissue located outside of a lactiferous duct of a breast by delivering electrical energy to the breast outside of the lactiferous duct. For example, the electrical ablation device 260 may be employed to treat breast cancer tissue 262 that is not located within a lactiferous duct 224 using electrical energy. FIG. 25 illustrates a cross-sectional view of a woman's breast 222. To treat a cancerous tissue 262 of a nonductal tumor, first and second needle electrodes 264a,b are located into the tumor target site 266 directly. In one embodiment, the first and second electrodes 264a,b are adapted to receive an electrical field such as, for example, an IRE waveform from an IRE generator. In another embodiment, the first and second electrodes 264a,b are adapted to receive a RF waveform from an RF generator. In one embodiment, IRE pulses may be applied to the target site 266 to destroy the cancerous tissue 262. A pulse train 268 comprising 20 to 40 pulses of ±500 to ±700 VDC of approximately 0.4 milliseconds in duration each is sufficient to destroy the cancerous tissue 226. As previously discussed, in one embodiment, the polarity of the electrical pulses may be inverted or reversed by the electrical waveform generator 14 during the treatment process.

FIG. 30 illustrates one embodiment of an electrical ablation device 261 to treat diseased tissue within a breast by delivering electrical energy to a space defined within the breast. For example, the electrical ablation device 261 may be employed to treat breast cancer tissue in a target site 269 within a certain depth of a space 267 formed within a breast 222 defined by a lumpectomy procedure. A needle electrode 263 is located into the space 267 transcutaneously through the breast 222. The needle electrode 263 comprises an inflatable and deflatable balloon member 265a, or a sponge-type member, disposed at a distal end portion of the needle electrode 263. The balloon member 265a comprises at least one radially expandable hollow body. At least one electrode surface contact member is disposed at a peripheral portion of the hollow body. The needle electrode 263 is particularly suited for use in treating diseased tissue, such as cancerous tissue, located within a certain depth or margin into the breast 222 adjacent to or surrounding the space 267. The inflatable and deflatable balloon member 265a may be introduced into the space 267 through a central lumen defined in the needle electrode 263. The balloon member 265a is inflatable to form an electrode suitable to couple electrical fields to destroy tissue to a predetermined depth surrounding the space 267 in the target site 269, creating a margin. The balloon member 265a may be formed as a hollow body which may be inflated by a suitable liquid, such as a solution of NaCl, so as to expand radially into contact with the inner wall of the space 267. At the outer periphery of the hollow body there may be disposed a plurality of discrete electrode surface contact members, which may be evenly distributed around the circumference of the hollow body for making proper electrical contact with the inner wall of the space 267. The electrode surface contact members may be connected in parallel or individually to the electrical waveform generator 14 through a first lead 234a running internally or externally of the needle electrode 263.

A pad electrode 265b comprising an electrically conductive pad is located on an exterior or outside portion 232 of the breast 222. The pad electrode 265b has a much larger surface area than the balloon member 265a of the needle electrode 263. In one embodiment, the balloon member 265a of the needle electrode 263 and the pad electrode 265b are adapted to receive an electrical field generated by the electrical waveform generator 14. In one embodiment, the electrical field is in the form of an IRE waveform generated by an IRE generator. In another embodiment, the electrical field is in the form of a RF waveform generated by an RF generator. The needle electrode 263 is connected to the waveform generator 14 through a first lead 234a, and the pad electrode 265b is connected to the waveform generator through a second lead 234b. In the illustrated embodiment, the needle electrode 263 is connected to a positive output of the waveform generator 14, and the pad electrode 265b is connected to a negative output of the waveform generator 14. As previously discussed, the electrical waveform generator 14 is capable of generating high voltage pulse waveforms of various amplitude, frequency, and pulse duration. In other embodiments, the polarity of the needle electrode 263 and the pad electrode 265b may be inverted. Multiple pulses may be supplied to the needle electrode 263 and the pad electrode 265b to destroy cancerous tissue at a certain depth of the space 267 near the target zone 269. A pulse train 268 comprising 20 to 40 pulses of ±500 to ±700 VDC of approximately 0.4 milliseconds in duration each is sufficient to destroy the cancerous tissue 226. As previously discussed, in one embodiment, the polarity of the electrical pulses may be inverted or reversed by the electrical waveform generator 14 during the treatment process.

The techniques discussed above with reference to FIGS. 23, 24, 25, and 30 also may be implemented to deliver RF energy to ablate the cancerous tissue 226, or any electrical waveforms suitable to destroy diseased tissue cells at the treatment site.

Figure 26:
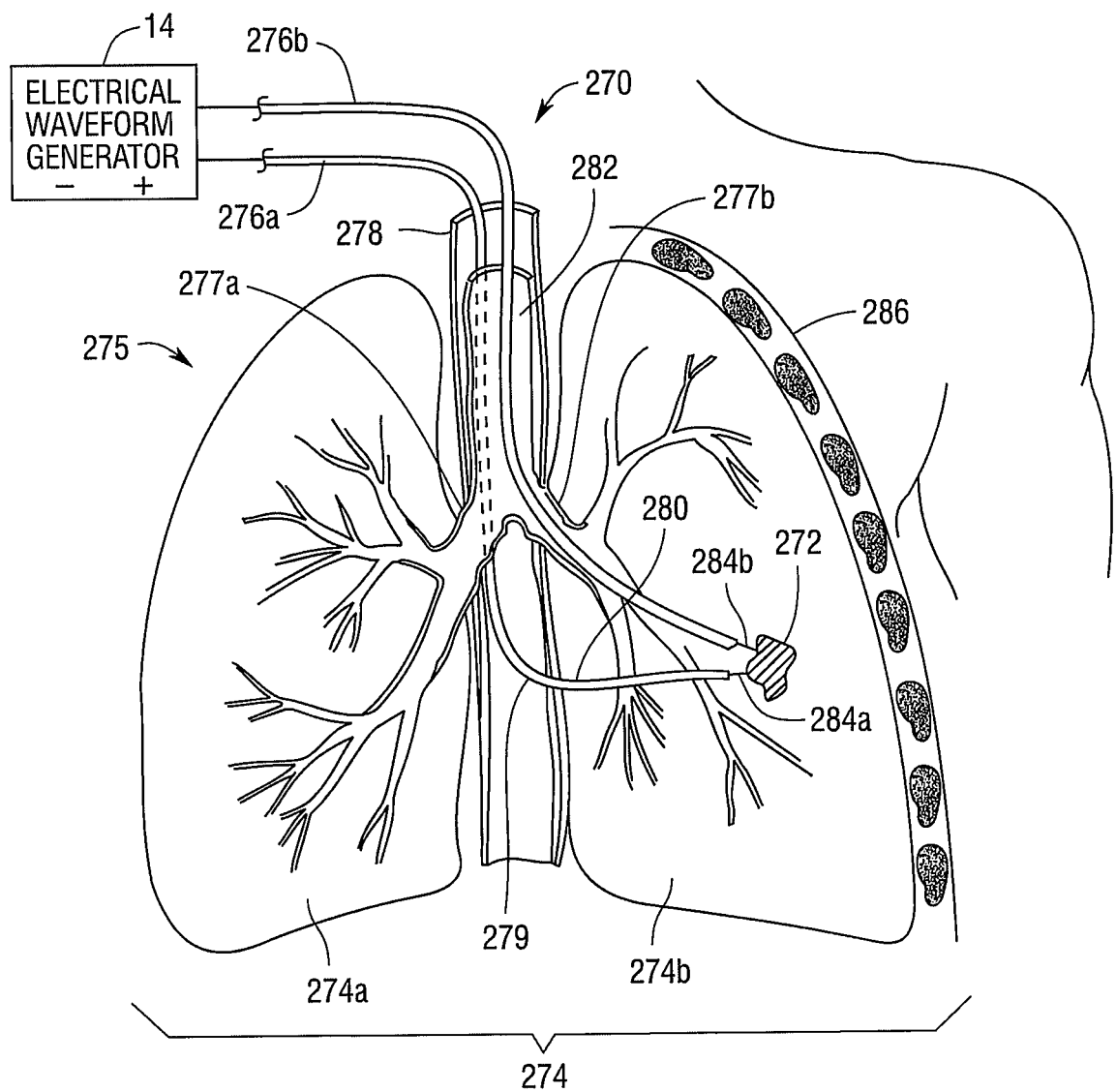
FIG. 26 illustrates one embodiment of an electrical ablation device to treat diseased tissue within a body cavity or organ by delivering electrical energy to the body cavity or organ.

FIG. 26 illustrates one embodiment of an electrical ablation device 270 to treat diseased tissue within a body cavity or organ by delivering electrical energy to the body cavity or organ. In the embodiment illustrated in FIG. 26, the electrical ablation device 270 is employed to treat tumors located in lungs 274. The embodiment, however, is not limited in this context and may be employed to treat tumors in any body cavity or organ. As illustrated in FIG. 26, the respiratory system 275 includes the trachea 282, which brings air from the nose or mouth into the right primary bronchus 277a and the left primary bronchus 277b. From the right primary bronchus 277a the air enters right lung 274a; from the left primary bronchus 277b the air enters the left lung 274b. The right lung 274a and the left lung 274b together form the lungs 274. The esophagus 278 extends into the thoracic cavity located behind the trachea 282 and the right and left primary bronchi 277a,b.

A lung tumor 272 is shown in the left lung 274b. The lung tumor 272 can be difficult to resect surgically. A first catheter 276a is introduced through a wall 279 of the esophagus 278, through lung tissue 280, and is located next to the tumor 272. A second catheter 276b is introduced through the trachea 282 and is located next to the tumor 272. The first and second catheters 276a,b are independently steerable. The first and second catheters 276a,b may be formed as hollow flexible tubes for insertion into a body cavity, duct, or vessel comprising first and second lumen to receive respective first and second elongated electrical conductors 284a,b therethrough. Each one of the first and second elongated electrical conductors 284a,b comprise a metal portion that extends beyond the distal end of the respective first and second catheters 276a,b. The proximal ends of the first and second electrical conductors 284a,b are coupled to the output electrodes of the waveform generator 14.

Electrical ablation by applying a suitable electrical field as discussed above is an effective way to destroy the lung tumor 272. In one embodiment, the first and second electrical conductors 284a,b are adapted to receive an IRE waveform from an IRE generator. In another embodiment, the first and second electrical conductors 284a,b are adapted to receive a RF waveform from an RF generator. Radio frequency ablation supplies energy into the cancerous tissue of the tumor 272 to raise its temperature and destroy the tumor 272. IRE employs high voltage DC pulses to destroy the tumor 272. The exposed metal portions of the electrical conductors 284a,b located within the respective first and second catheters 276a,b are located near the tumor 272, and high voltage DC pulses are applied to the cancerous tissue of the tumor 272 to destroy it. In one embodiment, the pulses may be extremely short in duration (~5 microseconds) and may be applied in multiple bursts such as 20 to 40 pulses, for example. The voltage amplitude or energy of each pulse is sufficient to cause damage to the cells at the target site (e.g., cancerous tissue forming the tumor 272) by necrosis or inducing apoptosis, as discussed above. Both the first and second catheters 276a,b may be introduced through the esophagus 278, the trachea 282, the skin 286 or any combination thereof. As previously discussed, in one embodiment, the polarity of the electrical pulses may be inverted or reversed by the electrical waveform generator 14 during the treatment process.

FIGS. 27, 28, and 29 illustrate one embodiment of an electrical ablation device 290 to treat diseased tissue within a body lumen using electrical energy. In the embodiment illustrated in FIGS. 27-29, the electrical ablation device is adapted to treat varicose veins. The embodiment, however, is not limited in this context. Reflux disease of the Greater Saphenous Vein (GSV) can result in a varicose vessel 292 as illustrated in FIG. 29. Conventional treatment techniques for varicose veins include stripping the vessel 292 and applying either chemical or thermal ablation to the vessel 292. The electrical ablation device 290 applies high voltage DC pulses to destroy a wall 294 of the vessel 292 and subsequently thermally seal the vessel 292. FIG. 27 illustrates a sectioned view of one embodiment of an electrical ablation probe 296.

FIG. 28 illustrates an end view of one embodiment of the electrical ablation probe 296. FIG. 29 is a cross-sectional view of one embodiment of the electrical ablation device 290 that may be inserted in a lumen 298 within the vessel or varicose vessel 292.

With reference to FIGS. 27-29, the probe 296 comprises a cannula or lumen 300 extending longitudinally therethrough. The distal end 298 of the probe 296 comprises first and second ring electrodes 302a,b at a potential difference. The first and second ring electrodes 300a,b are coupled to positive and negative electrodes or terminals of the electrical waveform generator 14 through first and second conductors 304a,b extending through respective conduits 306a,b formed within the probe 296 and extending longitudinally therethrough. The first and second conductors 304a,b may be electrically coupled to the first and second ring electrodes 302a,b in any suitable manner. The first and second ring electrodes 302a,b are adapted to receive an electrical field from a suitable generator. In one embodiment, the first and second ring electrodes 302a,b are adapted to receive an electrical field from a generator such as IRE waveform from an IRE generator. In another embodiment, the first and second ring electrodes 302a,b are adapted to receive an electrical field from a generator such as a RF waveform from an RF generator.

The electrical ablation probe 296 has a form factor that is suitable to be located into a tapered lumen 298 of the vessel 292. The probe 296 engages the vessel wall 294 as it is inserted within the tapered lumen 299 of the vessel 292. Suction 306 applied at a proximal end of the probe 296 draws a vacuum within the lumen 300 of the probe causing the vessel 292 to collapse at the distal end 298 of the probe 296.

Once the vessel 292 is collapsed or pulled down by the suction 306, a first pulse train 302 comprising high voltage DC pulses of a first amplitude $A_1$ (e.g., ~1 KV amplitude) and a first pulse duration $T_1$ (e.g., ~50 microseconds) is applied to the first and second ring electrodes 300a,b by the electrical waveform generator 14. The high voltage DC pulse train 302 eventually causes the cells to die. A second pulse train 304 having a lower voltage amplitude $A_2$ (e.g., ~500 VDC) and a second pulse duration $T_2$ (e.g., ~15 milliseconds) is applied to the first and second ring electrodes 300a,b of the probe 296 to cause thermal damage and thermally seal the vein 292. As previously discussed, in one embodiment, the polarity of the electrical pulses may be inverted or reversed by the electrical waveform generator 14 during the treatment process.

FIGS. 31-35 illustrates various embodiments of electrical ablation surgical instruments comprising a cutting device. Various embodiments of electrical ablation devices 400, 500, 600, and 700 are illustrated in FIGS. 31-35. These electrical ablation devices 400, 500, 600, and 700 are substantially analogous to the electrical ablation device 120 shown in FIGS. 12-18 and are operable with the handle 170 shown in FIGS. 17 and 18. Each of the electrical ablation devices 400, 500, 600, and 700, however, comprises a cutting device at a distal end. The cutting device can be employed to transect tissue. The types of tissue that may be transected with the cutting device include vessels, such as blood vessels, for example. It will be appreciated that the terms "proximal" and "distal" are used herein with reference to a clinician gripping the handle assembly 170 of the electrical ablation devices 400, 500, 600, and 700. Thus, a clamp jaw portion is distal with respect to the more proximal handle assembly 170. However, electrical ablation devices are used in many orientations and positions, and these terms are not intended to be limiting and absolute.

FIG. 31 is a perspective side view of one embodiment of an electrical ablation device 400 comprising a cutting blade 402.

The electrical ablation device 400 comprises an elongated flexible portion 422 and a clamp jaw portion 424. The clamp jaw portion 424 may be employed to thermally seal and cut tissue without exchanging instruments through a working channel of an endoscope, for example. In the embodiment illustrated in FIG. 31 the clamp jaw portion 424 is shown in an open position as indicated by arrow 456. The clamp jaw portion 424 comprises a first jaw member 426a and a second jaw member 426b. Inner portions of the first and second jaw members 426a,b may comprise a plurality of serrations 452a,b or teeth suitable to grasp targeted tissue between the first and second jaw members 426a,b. In the illustrated embodiment, the cutting blade 402 is located at the distal end of the second jaw member 426b. The cutting blade 402 is slidably movable in the directions indicated by arrows 408 and 410 within first and second slots 406a,b formed in the respective first and second jaw members 426a,b. A proximal end of the cutting blade 402 comprises a sharpened metal cutting edge 404 suitable to transect tissue. In one embodiment, the sharpened metal cutting edge 404 of the cutting blade 402 knife also comprises a razor sharp feature on its most distal surface. In the embodiment illustrated in FIG. 31, the cutting blade 402 is initially positioned at a distal end of the second jaw member 426b and is slidably moveable in the proximal direction indicated by arrow 408. Tissue grasped between the first and second jaw members 426a,b may be transected by slidably moving the cutting blade 402 from the distal end to the proximal end of the clamp jaw portion 424 in the direction indicated by arrow 408.

The first jaw member 426a comprises a first electrode portion 434a (not shown) and a first electrical insulator portion 436a (not shown). The first electrode portion 434a and the first electrical insulator portion 436a are analogous to the respective first electrode portion 134a and the first electrical insulator portion 136a shown in FIGS. 13 and 15. The second jaw member 426b comprises a second electrode portion 434b and a second electrical insulator portion 436b. The first and second electrode portions 434a,b comprise electrically conductive surfaces adapted to receive an electrical field from the electrical waveform generator 14. The first and second electrode portions 434a,b may function in monopolar or bipolar mode based on the operational mode of the electrical waveform generator 14. The cutting blade 402 is electrically insolated from the first and second electrode portions 434a,b.

In the illustrated embodiment, the clamp jaw portion 424 is substantially analogous to the clamp jaw portion 124 discussed above with reference to FIGS. 12-16. In one embodiment, the first jaw member 426a and the second jaw member 426a are pivotally coupled to a clevis 430 by respective first and second clevis pins 432a and 432b (not shown). The first and second jaw members 426a,b are pivotally movable relative to each other about a pivot point formed by the clevis 430. The first jaw member 426a is coupled to an actuator 440 by a first link 438a. The second jaw member 426b is coupled to an actuator 440 by a second link 438b. The elongated portion 422 comprises an elongated flexible member 446 coupled to the clevis 430 by a bushing coupler 442 and a ring capture 444. In one embodiment, the elongated flexible member 446 comprises a flat spring coil pipe for flexibility. A multi-lumen elongated flexible member 448 is disposed within the elongated flexible member 446.

The first and second jaw members 426a,b are operatively coupled to the actuator 440 via an elongated actuator member 450. The first and second jaw members 426a,b cooperate and act like forceps or tongs with paddle-like graspers to grasp and engage targeted tissue with the serrations 452a,b. The serrations 452a,b also hold tissue in place between the first and second jaw members 426*a,b* during the sealing and cutting operations. The elongated actuator member 450 is provided within one of the lumens formed within the multi-lumen elongated flexible member 448. The elongated actuator member 450 may be formed as a solid rod or a tube. The elongated actuator member 450 is coupled to the actuator 440 and is reciprocally movable in the directions indicated by arrows 454 and 458 to respectively open and close the first and second jaw members 426*a,b*. When the elongated actuator member 450 is moved in the direction indicated by arrow 454, the first and second jaw members 426*a,b* open in the direction indicated by arrow 456. When the elongated actuator member 450 is moved in the direction indicated by arrow 458, the first and second jaw members 426*a,b* close in the direction indicated by arrow 460.

With reference now to FIGS. 17, 18, and 31, in one embodiment, the electrical ablation device 400 may be operatively coupled to the handle assembly 170. As previously discussed, the handle assembly 170 comprises a base handle portion 172, a trigger 174, a rotation knob 176, and an opening 178. The opening 178 is to receive the distal end of the elongated actuator member 450. The trigger 174 is operatively coupled to the elongated actuator member 450. When the trigger 174 is pivotally moved (e.g., squeezed) in the direction indicated by arrow 180, the elongated actuator member 450 moves in the direction indicated by arrow 158, and the first and second jaw members 426*a,b* close in the direction indicated by arrow 460. When the trigger 174 is pivotally moved (e.g., released) in the direction indicated by arrow 182, the elongated actuator member 450 moves in the direction indicated by arrow 454, and the first and second jaw members 426*a,b* open in the direction indicated by arrow 456. The distal end of the elongated actuator member 450 is received within a neck portion 198 of the rotation knob 176. When the rotation knob 176 is rotated in the direction indicated by arrow 194 the electrical ablation device 400 is also rotated in the direction indicated by arrow 194. When the rotation knob 176 is rotated in the direction indicated by arrow 196 the electrical ablation device 400 also is rotated in the direction indicated by arrow 196.

First and second electrical conductors 418*a,b* are electrically coupled to the respective first and second electrode portions 434*a,b* formed in the respective first and second jaw members 426*a,b*. In one embodiment, the first and second electrode portions 434*a,b* have a substantially flat paddle-like shape. The first and second electrical conductors 418*a,b* may be received through lumens formed in the multi-lumen elongated flexible member 448 and are coupled to the first and second electrode portions 434*a,b* in any suitable manner. A switch may be coupled to the electrical conductors 418*a,b* to activate and deactivate the first and second electrode portions 434*a,b*. As described in more detail below, activating the first and second electrode portions 434*a,b*, for example, thermally seals the tissue, e.g., a blood vessel, held between the first and second jaw members 426*a,b*.

In one embodiment, the first and second electrode portions 434*a,b* are adapted to receive an electrical field such as an IRE waveform from a suitable IRE waveform generator. In another embodiment, the first and second electrode portions 434*a,b* are adapted to receive a RF waveform from a suitable RF waveform generator. In one embodiment, the first and second electrode portions 434*a,b* are connected to the electrical waveform generator 14 such as a high voltage DC waveform generator (±500 VDC), for example. It has been shown that when high electric fields are applied to tissue, the cell membrane will form an aqueous pathway through which molecules can flow (electroporation). If the electric field is increased to a sufficient level, the wall of the cell will rupture and subsequent apoptosis/necrosis will occur (irreversible electroporation). This occurs on the order of 1 millisecond, therefore very little energy is put into the tissue and very little heating occurs. Therefore, the tissue can be treated more precisely and safely with the electrical ablation device 400 than complete removal or thermal destruction of the diseased mucosal tissue. As previously discussed, in one embodiment, the polarity of the electrical pulses may be inverted or reversed by the electrical waveform generator 14 during the treatment process.

In one embodiment, the electrical ablation device 400 may be employed to thermally seal and transect targeted tissue. Targeted tissue may include a variety of vessels, for example. The targeted tissue is grasped between the first and second jaw members 426*a,b*. The tissue is sealed by supplying electrical energy from the electrical waveform generator 14 to the first and second electrode portions 434*a,b*. The electrical waveform generator 14 may supply electrical energy either in bipolar or monopolar form. The thermally sealed tissue is transected by actuating the cutting blade 402 such that the cutting blade 402 slidably moves in the proximal direction indicated by arrow 408. In one embodiment, the electrical ablation device 400 may be employed to grab and place thermal seals on a desired vessel, for example. Once an adequate amount of seals are applied to the vessel and hemostasis is believed to have been achieved, the vessel may be cut. To cut the vessel, the electrical ablation device 400 may be employed to grab the vessel again at the desired cut location. While the vessel is located within the first and second jaw members 426*a,b* the cutting lade 402 would be retracted proximally in the direction indicated by arrow 408 to transect the vessel.

In one embodiment, the cutting blade 402 may be employed to bluntly dissect the targeted tissue away from thicker more vascular masses of tissue, such as vascular tissue surrounding a blood vessel. The blunt dissection may be performed with or without energy assistance. In one embodiment, the electrical waveform generator 14 may be electrically coupled to the cutting blade 402 to assist the cutting action. Accordingly, the cutting blade 402 may be coupled to the monopolar output of the electrical waveform generator 14, or to a conventional monopolar electrosurgical generator, to assist the cutting action of the cutting blade 402. The bluntly dissected tissue may be thermally sealed by grasping the tissue between the first and second jaw members 426*a,b* and applying monopolar or bipolar electrical energy to the first and second electrode portions 434*a,b*. A control switch may be provided on the handle assembly 170 to facilitate switching the energy supply to the cutting blade 402 and to the first and second electrode portions 434*a,b*. Once the tissue is sealed, the cutting blade 402 may be slidably moved within the first and second slots 406*a,b* in the proximal direction indicated by arrow 408 to transect the tissue. Once the tissue is transected, the cutting blade 402 can be moved distally in the direction indicated by arrow 410 to prepare for sealing and cutting other tissues. The embodiments are limited in this context.

FIG. 32 is a perspective side view of one embodiment of an electrical ablation device 500 comprising a cutting blade 502. The electrical ablation device 500 comprises an elongated flexible portion 422 and a clamp jaw portion 524. The clamp jaw portion 524 may be employed to thermally seal and cut tissue without exchanging instruments through a working channel of an endoscope, for example. In the illustrated embodiment, the clamp jaw portion 524 is substantially analogous to the clamp jaw portion 124 discussed above with reference to FIGS. 12-18, and is substantially analogous to the clamp jaw portion 424 discussed above with respect to FIG. 31. The clamp jaw portion 524 is shown in an open position as indicated by arrow 556. The clamp jaw portion 524 comprises a first jaw member 526a and a second jaw member 526b. Inner portions of the first and second jaw members 526a,b may comprise a plurality of serrations 552a,b or teeth suitable to grasp tissue between the first and second jaw members 526a,b. In the illustrated embodiment, the cutting blade 502 is located at the proximal end of the second jaw member 526b. The cutting blade 502 is slidably movable in the directions indicated by arrows 408 and 410 within first and second slots 506a,b formed in the respective first and second jaw members 526a,b. A distal end of the cutting blade 502 comprises a sharpened metal cutting edge 504 suitable to transect tissue. In the embodiment illustrated in FIG. 31, the cutting blade 502 is initially positioned at a proximal end of the second jaw member 526b and is slidably moveable in a distal direction as indicated by arrow 410. Tissue held between the first and second jaw members 526a,b may be transected by slidably moving the cutting blade 502 from the distal end to the proximal end of the clamp jaw portion 524.

The first jaw member 526a comprises a first electrode portion 534a (not shown) and a first electrical insulator portion 536a (not shown). The first electrode portion 534a and the first electrical insulator portion 536a are analogous to the first electrode portion 134a and the first electrical insulator portion 136a shown in FIGS. 13 and 15. The second jaw member 526b comprises a second electrode portion 534b and a second electrical insulator portion 536b. The first and second electrode portions 534a,b comprise electrically conductive surfaces adapted to receive an electrical field from the electrical waveform generator 14. The first and second electrode portions 534a,b may function in monopolar or bipolar mode based on the operational mode of the electrical waveform generator 14. The cutting blade 502 is electrically insolated from the first and second electrodes 534a,b.

In one embodiment, the electrical ablation device 500 may be employed to thermally seal and transect targeted tissue. Targeted tissue may include a variety of vessels, for example. The targeted tissue is grasped between the first and second jaw members 526a,b. The targeted tissue is sealed by supplying electrical energy from the electrical waveform generator 14 to the first and second electrode portions 534a,b. The electrical waveform generator 14 may supply electrical energy either in bipolar or monopolar form. The thermally sealed tissue is transected by actuating the cutting blade 502 such that the cutting blade 502 slidably moves in the distal direction indicated by arrow 410.

In one embodiment, the cutting blade 502 may be employed to bluntly dissect the targeted tissue away from thicker more vascular masses of tissue such as vascular tissue surrounding a blood vessel, for example. The blunt dissection may be performed with or without energy assistance. In one embodiment, the electrical waveform generator 14 may be electrically coupled to the cutting blade 502 to assist the cutting action. Accordingly, the cutting blade 502 may be coupled to the monopolar output of the electrical waveform generator 14, or to a conventional monopolar electrosurgical generator, to assist the cutting action of the cutting blade 502. The bluntly dissected tissue may be thermally sealed by grasping the tissue between the first and second jaw members 526a,b and applying monopolar or bipolar electrical energy to the first and second electrode portions 534a,b. A control switch may be provided on the handle assembly 170 to facilitate switching the energy supply to the cutting blade 502 and to the first and second electrode portions 534a,b. Once the tissue is sealed, the cutting blade 502 may be slidably moved within the first and second slots 506a,b in the distal direction indicated by arrow 408 to transect the tissue. Once the tissue is transected, the cutting blade 502 can be moved proximally in the direction indicated by arrow 408 to prepare for sealing and cutting other tissues. The embodiments are limited in this context.

FIG. 33 is a perspective side view of one embodiment of an electrical ablation device 600 comprising a cutting blade 602. The electrical ablation device 600 comprises an elongated flexible portion 422 and a clamp jaw portion 624. The clamp jaw portion 624 may be employed to thermally seal and cut tissue without exchanging instruments through a working channel of an endoscope, for example. The electrical ablation device 600 is substantially analogous to the electrical ablation device 120 shown in FIGS. 12-18, and the clamp jaw portion 624 is substantially analogous to the clamp jaw portion 424 discussed above with respect to FIGS. 31 and 32. In the illustrated embodiment, the clamp jaw portion 624 is shown in an open position as indicated by arrow 456. The clamp jaw portion 624 comprises first and second jaw members 626a,b. Inner portions of the first and second jaw members 626a,b may comprise a plurality of serrations 652a,b or teeth suitable to grasp targeted tissue between the first and second jaw members 626a,b.

The first jaw member 626a comprises a first electrode portion 634a (not shown) and a first electrical insulator portion 636a (not shown). The second jaw member 626b comprises a second electrode portion 634b and a second electrical insulator portion 636b. The first electrode portion 634a and the first electrical insulator portion 636a are analogous to the first electrode portion 134a and the first electrical insulator portion 136a shown in FIGS. 13 and 15. The first and second electrode portions 634a,b comprise electrically conductive surfaces adapted to receive an electrical field from a suitable waveform generator. In the embodiment illustrated in FIG. 33, the cutting blade 602 is formed as a thermal cutting blade. The geometry of the first and second electrode portions 634a,b is defined to thermally seal and cut tissue located between the first and second jaw members 626a,b. In one embodiment, the second electrode portion 634b comprises a long, narrow ridge 603 extending longitudinally along the second electrode portion 634b. The ridge 603 rises above substantially flat portions 606a,b of the second electrode portion 634a,b at an angle to define an edge 604 at a high point thereof. The edge 604 extends longitudinally along the length of the ridge 603. Electrical energy density is concentrated at the edge 604 of the ridge 603 because the surface area of the edge 604 in contact with the tissue is minimized. In one embodiment, the edge 604 may be sharpened to further enhance the cutting ability of the second electrode portion 634b. The ridge 603 and the substantially flat portions 606a,b of the second electrode portion 634b are suitable for thermally sealing and cutting tissue, e.g., vessels, grasped between the first and second jaw members 626a,b. The first and second electrode portions 634a,b may be driven in either monopolar or bipolar mode. The cutting blade 602 is electrically insolated from the first and second electrode portions 634a,b.

FIG. 34 is a perspective side view of one embodiment of an electrical ablation device 700. The electrical ablation device 700 comprises an elongated flexible portion 422 and a clamp jaw portion 724. The clamp jaw portion 724 may be employed to thermally seal and cut tissue, e.g., a vessel, without exchanging instruments through a working channel of an endoscope, for example. The electrical ablation device 700 is substantially analogous to the electrical ablation device 120 shown in FIGS. 12-18, and the clamp jaw portion 724 is substantially analogous to the clamp jaw portion 424 discussed above with respect to FIGS. 31-33. In the illustrated embodiment, the clamp jaw portion 724 is shown in an open position as indicated by arrow 456. The clamp jaw portion 724 comprises first and second jaw members 726a,b. Inner portions of the first and second jaw members 726a,b may comprise a plurality of serrations 752a,b or teeth suitable to grasp targeted tissue between the first and second jaw members 726a,b. The serrations 752b are positioned substantially along a centerline axis "A" extending longitudinally along the length of the second jaw member 726b. Thus, in the illustrated embodiment, the serrations 752b are positioned away from the outside edges of the sealing surfaces 704a,b of the second jaw member 726b and extend along the inner surface.

The first jaw member 726a comprises a first electrode portion 734a (not shown) and a first electrical insulator portion 736a (not shown). The second jaw member 726b comprises a second electrode portion 734b and a second electrical insulator portion 736b. The first electrode portion 734a and the first electrical insulator portion 736a are analogous to the first electrode portion 134a and the first electrical insulator portion 136a shown in FIGS. 13 and 15. In one embodiment, the centerline serrations 752b limit damage to the tissue on the outside edges of the sealing surfaces 704a,b. In one embodiment, the serrations 752b may be formed with a sharp cutting edge to cut tissue within the first and second jaw members 726a,b.

In one embodiment, the handle assembly 170 may comprise several control positions. A first control position closes the first and second jaw members 726a,b on the targeted tissue, holding it in place with minimal compression. Energy may be activated to provide hemostasis of the tissue within the first and second jaw members 726a,b. The handle assembly 170 then may be activated to a second control position to apply greater compression force against the tissue. The greater force may be sufficient to cut or sever the tissue along the center line serrations 752b.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although the various embodiments have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An electrical ablation device, comprising:
   an elongated flexible member having a proximal end and a distal end, the elongated flexible member comprising a flat spring coil pipe;
   a multi-lumen elongated flexible member located within the elongated flexible member;
   a clamp jaw portion located at the distal end of the elongated flexible member, the clamp jaw portion operatively movable from an open position to a closed position; and
   a fixed cutting blade located in the clamp jaw portion, the cutting blade comprising a cutting edge facing in a proximal direction;
   wherein the clamp jaw portion is adapted to couple to an electrical waveform generator and to receive an electrical waveform.

2. The electrical ablation device of claim 1, wherein the cutting blade comprises a plurality of serrations.

3. The electrical ablation device of claim 2, wherein the plurality of serrations extend along a longitudinal axis positioned away from outside edges of the clamp jaw portion.

4. The electrical ablation device of claim 1, wherein the clamp jaw portion comprises pivotally coupled first and second jaw members, the first and second jaw members comprising respective first and second electrode portions formed on an inner surface thereof to couple to the electrical waveform generator.

5. An electrical ablation device, comprising:
   an elongated flexible member having a proximal end and a distal end, the elongated flexible member comprising a flat spring coil pipe;
   a multi-lumen elongated flexible member located within the elongated flexible member;
   pivotally coupled first and second jaw members located at the distal end of the elongated flexible member, the first and second jaw members comprising respective first and second electrode portions formed on an inner surface thereof to couple to an electrical waveform generator, the first and second jaw members operatively movable from an open position to a closed position; and a fixed cutting blade formed on at least one of the first and second jaw members, the cutting blade comprising a cutting edge facing in a proximal direction;
wherein the first and second jaw members are adapted to couple to the electrical waveform generator and the first and second electrode portions are adapted to receive an electrical waveform.

6. The electrical ablation device of claim 5, wherein the cutting blade comprises a plurality of serrations.

7. The electrical ablation device of claim 6, wherein the plurality of serrations extend along a longitudinal axis positioned away from outside edges of the second jaw member.

8. A surgical device, comprising:
an elongated flexible member having a proximal end and a distal end, the elongated flexible member comprising a flat spring coil pipe;
a multi-lumen elongated flexible member located within the elongated flexible member;
pivotally coupled first and second jaw members attached to the distal end of the elongated flexible member; and
a plurality of serrations fixably disposed on an inner surface of at least one of the first and second jaw members, the plurality of serrations positioned substantially along a centerline axis extending longitudinally along a length of the respective first or second jaw member, the plurality of serrations comprising a proximally facing cutting edge formed on a proximal most serration.

9. The surgical device of claim 8, wherein the plurality of serrations are disposed on the respective inner surfaces of the first and second jaw members.

10. The surgical device of claim 8, wherein the plurality of serrations comprises a cutting edge.

11. The surgical device of claim 9, comprising:
a first electrode disposed on the inner surface of the first jaw member between the plurality of serrations of the first jaw member and an outer edge of the first jaw member, the first electrode to receive an electrical waveform from a waveform generator.

12. The surgical device of claim 11, comprising:
a second electrode disposed on the inner surface of the second jaw member between the plurality of serrations of the second jaw member and an outer edge of the second jaw member, the second electrode to receive the electrical waveform from the waveform generator.

13. The surgical device of claim 12, comprising:
a handle portion attached to the proximal end of the elongated flexible member, the handle portion in communication with the first and second jaw members and comprising a trigger pivotally manipulatable to vary a relative position of the first and second jaw members.

14. The surgical device of claim 13, wherein the handle portion comprises a first control position to place the first and second jaws members in a first treatment position relative to targeted tissue, wherein the first and second jaw members compressibly retain the tissue when in the first treatment position such that the tissue is contacted by the first and second electrodes, and such that the tissue is not severed by the plurality of serrations.

15. The surgical device of claim 14, wherein the handle portion comprises a second control position to place the first and second jaws members in a second treatment position relative to the tissue, wherein the first and second jaw members apply a compressive force to the tissue when in the second treatment position such that the targeted tissue is severed by the plurality of serrations.

16. The surgical device of claim 8, comprising:
a clevis coupled to a distal end of the elongated flexible member;
at least one lumen formed within the flexible member;
an elongated actuator member slidably disposed within the at least one lumen, wherein the elongated actuator member comprises a distal end coupled to the clevis, wherein slidably moving the elongated actuator member in a first direction pivotably moves the first and second jaw members apart, and wherein slidably moving the elongated actuator member in a second direction pivotably closes the first and second jaw members to define a first treatment position for applying a first compressive force and a second treatment position for applying a second compressive force, wherein the second compressive force is greater than the first compressive force;
a cutting blade located in the clamp jaw portion, the cutting blade comprising a cutting edge facing in a proximal direction; and
a handle portion comprising a trigger, the handle portion coupled to a proximal end of the elongated actuator member;
wherein the trigger is pivotally moveable to move the elongated actuator member in the first and second directions.

17. A system, comprising:
a surgical instrument, comprising:
an elongated flexible member having a proximal end and a distal end, the elongated flexible member comprising a flat spring coil pipe;
a multi-lumen elongated flexible member located within the elongated flexible member;
pivotally coupled first and second jaw members attached to the distal end of the elongated flexible member;
a plurality of serrations fixably disposed on respective inner surfaces of the first and second jaw members, the plurality of serrations positioned substantially along a centerline axis extending longitudinally along a length of the second jaw member, the plurality of serrations comprising a proximally facing cutting edge formed on a proximal most serration;
a first electrode disposed on the inner surface of the first jaw member between the plurality of serrations of the first jaw member and an outer edge of the first jaw member; and
a second electrode disposed on the inner surface of the second jaw member between the plurality of serrations of the second jaw member and an outer edge of the second jaw member; and
a waveform generator electrically coupled to the surgical instrument for selectively applying an electrical waveform to the first and second electrodes.

18. The system of claim 17, wherein the surgical instrument comprises a handle portion attached to the proximal end of the elongated flexible member, the handle portion in communication with the first and second jaw members and comprising a trigger pivotally manipulatable to vary a relative position of the first and second jaw members.

19. The system of claim 18, wherein the handle portion comprises a first control position to place the first and second jaws members in a first treatment position relative to targeted tissue, wherein the first and second jaw members compressibly retain the tissue when in the first treatment position such that the tissue is contacted by the first and second electrodes, and such that the tissue is not severed by the plurality of serrations.

20. The system of claim 19, wherein the handle portion comprises a second control position to place the first and second jaws members in a second treatment position relative to the tissue, wherein the first and second jaw members apply a compressive force to the tissue when in the second treatment position such that the tissue is severed by the plurality of serrations.

21. The system of claim 17, wherein the surgical instrument comprises:
- a clevis coupled to a distal end of the elongated flexible member;
- at least one lumen formed within the flexible member;
- an elongated actuator member slidably disposed within the at least one lumen, wherein the elongated actuator member comprises a distal end coupled to the clevis, wherein slidably moving the elongated actuator member in a first direction pivotably moves the first and second jaw members apart, and wherein slidably moving the elongated actuator member in a second direction pivotably closes the first and second jaw members to define a first treatment position for applying a first compressive force and a second treatment position for applying a second compressive force, wherein the second compressive force is greater than the first compressive force;
- a handle portion comprising a trigger, the handle portion coupled to a proximal end of the elongated actuator member;
- wherein the trigger is pivotally moveable to move the elongated actuator member in the first and second directions.

* * * * *

UNITED STATES PATENT AND TRADEMARK OFFICE
CERTIFICATE OF CORRECTION

PATENT NO.       : 8,568,410 B2                                                         Page 1 of 1
APPLICATION NO. : 12/109673
DATED            : October 29, 2013
INVENTOR(S)      : Vakharia et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1420 days.

Signed and Sealed this
Twenty-third Day of May, 2017

Michelle K. Lee
*Director of the United States Patent and Trademark Office*